(12) United States Patent
Choo et al.

(10) Patent No.: US 9,663,464 B2
(45) Date of Patent: May 30, 2017

(54) CARBAZOLE DERIVATIVES ACTING ON 5-HT7 RECEPTOR

(71) Applicant: KOREA INSTITUTE OF SCIENCE AND TECHNOLOGY, Seoul (KR)

(72) Inventors: Hyunah Choo, Seoul (KR); Gyo Chang Keum, Seoul (KR); Youngjae Kim, Seoul (KR); Mi Young Yeom, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 14/629,821

(22) Filed: Feb. 24, 2015

(65) Prior Publication Data

US 2016/0244408 A1    Aug. 25, 2016

(51) Int. Cl.
| | |
|---|---|
| *C07D 403/06* | (2006.01) |
| *A61K 31/496* | (2006.01) |
| *C07D 209/86* | (2006.01) |
| *C07D 401/06* | (2006.01) |
| *C07D 413/06* | (2006.01) |

(52) U.S. Cl.
CPC ......... *C07D 209/86* (2013.01); *C07D 401/06* (2013.01); *C07D 403/06* (2013.01); *C07D 413/06* (2013.01)

(58) Field of Classification Search
None
See application file for complete search history.

(56) References Cited

FOREIGN PATENT DOCUMENTS

| | | | |
|---|---|---|---|
| WO | 97/29097 | A1 | 8/1997 |
| WO | 97/48681 | A1 | 12/1997 |
| WO | 97/49695 | A1 | 12/1997 |
| WO | 99/24022 | A2 | 5/1999 |
| WO | 00/00472 | A1 | 1/2000 |
| WO | 00/56712 | A1 | 9/2000 |
| WO | 03/048118 | A1 | 6/2003 |
| WO | 2010/033643 | * | 3/2010 |
| WO | 2013/185124 | A1 | 12/2013 |

OTHER PUBLICATIONS

Ferorelli et al., Design and Evaluation of Naphthol- and Carbazole-Containing Fluorescent ó Ligands as Potential Probes for Receptor Binding Studies, Journal of Medicinal Chemistry, Aug. 22, 2007, pp. 4648-4655, vol. 50.
Jose A. Terron ,Is the 5-HT 7 receptor involved in the pathogenesis and prophylactic treatment of migraine?, European Journal of Pharmacology, Feb. 22, 2002,1-11 page, vol. 439.
Timothy W. Lovenberg et al, A Novel Adenylyl Cyclase-Activating Serotonin Receptor (5-HT 7) Implicated in the regulation of Mammalian Circadian Rhythms,Neuron, Sep. 1993,449-458 page,vol. 11, cell press,La Jolla, California.
P. Schoeffter et al.,Functional, endogenously expressed 5-hydroxytryptamine 5-ht7 receptors in human vascular smooth muscle cells, British Journal of Pharmacology,1996, 993-994 page, vol. 117, Switzerland.

* cited by examiner

*Primary Examiner* — Emily Bernhardt
(74) *Attorney, Agent, or Firm* — Goldilocks Zone IP Law

(57) ABSTRACT

The present invention provides a carbazole derivative represented by Formula 1:

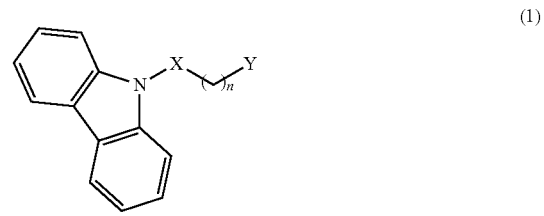

(1)

wherein X is $CH_2$ or $C(O)$, Y is selected from $NR_1R_2$, piperidinyl groups in which two of the carbon atoms are substituted with $R_3$ and $R_4$, piperazinyl groups in which the nitrogen atom is substituted with $R_5$, and morpholinyl groups, n is an integer from 2 to 5, $R_1$ and $R_2$, which may be identical or different, are each independently selected from $C_1$-$C_6$ alkyl, phenyl, and benzyl, with the proviso that $R_1$ and $R_2$ may be bonded together to form a ring, $R_3$ and $R_4$, which may be identical or different, are each independently selected from hydrogen, $C_1$-$C_6$ alkyl, phenyl, and benzyl, and $R_5$ is selected from $C_1$-$C_6$ alkyl, $C_1$-$C_4$ alkylcarbonyl, phenyl substituted with $C_1$-$C_4$ alkyloxy, hydroxyphenyl, benzyl, and benzoisoxazol-3-yl; or a pharmaceutically acceptable salt thereof.

5 Claims, 1 Drawing Sheet

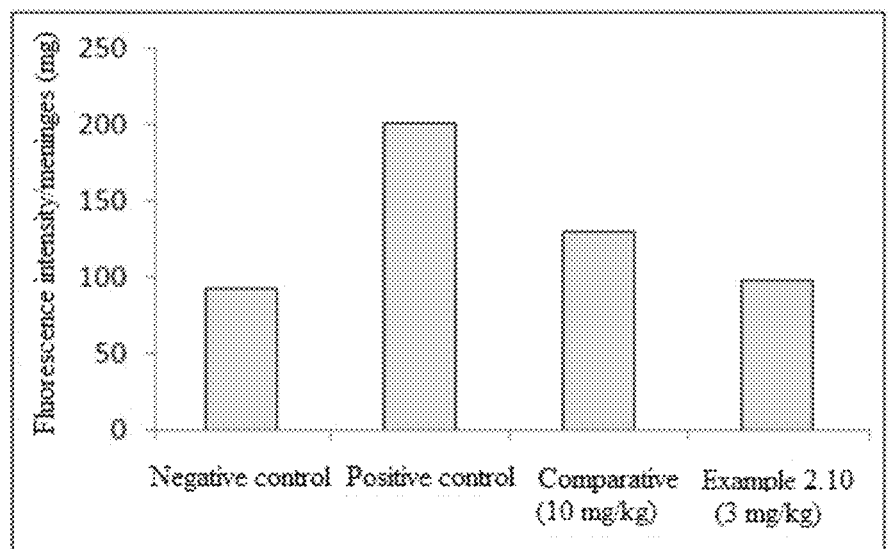

CARBAZOLE DERIVATIVES ACTING ON 5-HT7 RECEPTOR

CROSS-REFERENCE TO RELATED APPLICATIONS

This application claims priority under 35 U.S.C. §119 to Korean Patent Application No. 10-2014-0048074 filed on Apr. 22, 2014 in the Korean Intellectual Property Office, the disclosure of which is incorporated herein by reference in its entirety.

BACKGROUND OF THE INVENTION

1. Field of the Invention

The present invention relates to carbazole derivatives and pharmaceutically acceptable salts thereof that act on the $5\text{-}HT_7$ receptor, methods for preparing the compounds, and pharmaceutical compositions containing the compounds as active ingredients.

2. Description of the Related Art

The neurotransmitter serotonin acts on 14 different serotonin receptors distributed in various organs and is responsible for various physiological phenomena. Of these, the $5\text{-}HT_7$ subtype is the most recently cloned serotonin receptor and is known to be abundantly distributed, particularly in the hypothalamus, thalamus, hippocampus, and cortex. The $5\text{-}HT_7$ receptor is also found in peripheral tissues, such as spleen, stomach, intestine, and coronary artery, as well as in the brain tissues. Such expression patterns indicate that the $5\text{-}HT_7$ receptor is involved in various functions and pathologies. Particularly, the $5\text{-}HT_7$ receptor is known to perform important functions in thermoregulation, circadian rhythm, learning and memory, sleep, and hippocampal signal transduction (Lowenberg, T. N. et al., Neuron (1993) 11: 449-458). The $5\text{-}HT_7$ receptor is also known to be implicated in neurological diseases, such as depression, migraine, anxiety, and pain, particularly inflammatory pain and neuropathic pain (see a) Schoeffter, P. et al. Br J Pharmacol (1996) 117: 993-994; b) Terron, J. A., Eur. J. Pharmacol (2002) 439: 1-11).

Numerous efforts have been made so far to develop $5\text{-}HT_7$ receptor antagonists and agonists. However, only a few selective $5\text{-}HT_7$ receptor antagonists were reported. For example, International Patent Publication Nos. WO 97/48681, WO 97/29097, WO 97/49695, WO 00/56712, and WO 03/48118 disclose sulfonamide-based antagonists. Further, International Patent Publication Nos. WO 99/24022 and WO 00/000472 disclose tetrahydroisoquinoline derivatives acting on the $5\text{-}HT_7$ receptor.

Despite the research, a need still exists to find compounds that have selective pharmacological activities against the $5\text{-}HT_7$ receptor, achieving excellent pharmacological effects against $5\text{-}HT_7$ receptor-mediated diseases and conditions and good pharmaceutical properties in terms of administration, dispersion, uptake, distribution, metabolism, and excretion.

SUMMARY OF THE INVENTION

It is a first object of the present invention to provide carbazole derivatives and pharmaceutically acceptable salts thereof that act on the $5\text{-}HT_7$ receptor.

It is a second object of the present invention to provide methods for preparing the carbazole derivatives.

It is a third object of the present invention to provide pharmaceutical compositions which include the carbazole derivatives and the pharmaceutically acceptable salts thereof as active ingredients and are thus effective in treating or preventing central nervous system diseases, such as depression, migraine, anxiety, pain, inflammatory pain, neuropathic pain, body temperature dysregulation, circadian rhythm dysregulation, sleep disturbance, and smooth muscle-related diseases.

One aspect of the present invention provides a carbazole derivative represented by Formula 1:

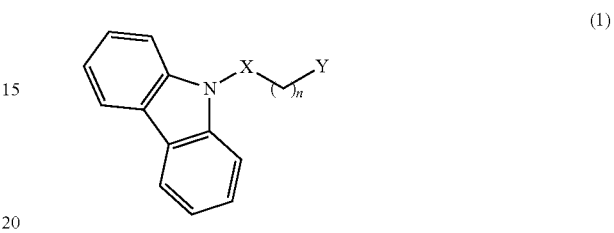

(1)

wherein X is $CH_2$ or $C(O)$, Y is selected from $NR_1R_2$, piperidinyl groups substituted with $R_3$ and $R_4$, piperazinyl groups in which the nitrogen atom is substituted with $R_5$, and morpholinyl groups, n is an integer from 2 to 5, $R_1$ and $R_2$, which may be identical or different, are each independently selected from $C_1\text{-}C_6$ alkyl, phenyl, and benzyl, with the proviso that $R_1$ and $R_2$ may be bonded together to form a ring, $R_3$ and $R_4$, which may be identical or different, are each independently selected from hydrogen, $C_1\text{-}C_6$ alkyl, phenyl, and benzyl, and $R_5$ is selected from $C_1\text{-}C_6$ alkyl, $C_1\text{-}C_4$ alkylcarbonyl, phenyl substituted with $C_1\text{-}C_4$ alkyloxy, hydroxyphenyl, benzyl, and benzoisoxazol-3-yl, or a pharmaceutically acceptable salt thereof; and a pharmaceutical composition including the carbazole derivative or pharmaceutically acceptable salt thereof as an active ingredient.

A further aspect of the present invention provides a method for preparing the carbazole derivative represented by Formula 1, including alkylating or acylating carbazole to prepare a carbazole intermediate and reacting the carbazole intermediate with a secondary amine compound.

Another aspect of the present invention provides a pharmaceutical composition for preventing and treating a central nervous system disease, including the carbazole derivative represented by Formula 1 or pharmaceutically acceptable salt thereof as an active ingredient.

The central nervous system disease may be selected from the group consisting of depression, migraine, anxiety, pain, inflammatory pain, neuropathic pain, body temperature dysregulation, circadian rhythm dysregulation, sleep disturbance, smooth muscle-related diseases, and combinations thereof.

The carbazole derivative and the pharmaceutically acceptable salt thereof according to the present invention exhibit high binding affinities for and antagonistic activities against the $5\text{-}HT_7$ serotonin receptor. Therefore, the pharmaceutical composition of the present invention, which includes the carbazole derivative or pharmaceutically acceptable salt thereof as an active ingredient, is effective in treating and preventing central nervous system diseases where antagonistic activities against $5\text{-}HT_7$ are required, such as depression, migraine, anxiety, pain, inflammatory pain, neuropathic pain, body temperature dysregulation, circadian rhythm dysregulation, sleep disturbance, and smooth muscle-related diseases.

BRIEF DESCRIPTION OF THE DRAWINGS

These and/or other aspects and advantages of the invention will become apparent and more readily appreciated from the following description of the embodiments, taken in conjunction with the accompanying drawings of which:

FIG. 1 shows the preventive effect of a compound prepared in Example 2.10 on migraine.

DETAILED DESCRIPTION OF THE INVENTION

The present invention will now be described in more detail.

In one aspect, the present invention provides a carbazole derivative represented by Formula 1:

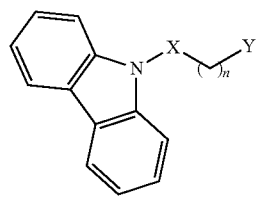

(1)

wherein X is $CH_2$ or $C(O)$, Y is selected from $NR_1R_2$, piperidinyl groups in which two of the carbon atoms are substituted with $R_3$ and $R_4$, piperazinyl groups in which the nitrogen atom is substituted with $R_5$, and morpholinyl groups, n is an integer from 2 to 5, $R_1$ and $R_2$, which may be identical or different, are each independently selected from $C_1$-$C_6$ alkyl, phenyl, and benzyl, with the proviso that $R_1$ and $R_2$ may be bonded together to form a ring, $R_3$ and $R_4$, which may be identical or different, are each independently selected from hydrogen, $C_1$-$C_6$ alkyl, phenyl, and benzyl, and $R_5$ is selected from $C_1$-$C_6$ alkyl, $C_1$-$C_4$ alkylcarbonyl, phenyl substituted with $C_1$-$C_4$ alkyloxy, hydroxyphenyl, benzyl, and benzoisoxazol-3-yl; or a pharmaceutically acceptable salt thereof.

When Y in Formula 1 is $NR_1R_2$, $R_1$ and $R_2$ may be bonded together to form a ring. In this case, Y may be, for example, a heterocyclic group selected from the group consisting of pyrrolidinyl, piperidinyl, and azepanyl. The heterocyclic group may be substituted with $C_1$-$C_5$ alkyl.

In the present invention, Y in Formula 1 may be particularly selected from, but not limited to, methylbutylaminyl, methylbenzylaminyl, pyrrolidinyl, azepanyl, morpholinyl, 4-methylpiperidinyl, 3-methylpiperidinyl, 3,5-dimethylpiperidinyl, 4-phenylpiperidinyl, 4-benzylpiperidinyl, 4-methylpiperazinyl, 4-acetylpiperazinyl, 4-(2-methoxyphenyl)piperazinyl, 4-(2-hydroxyphenyl)piperazinyl, 4-benzylpiperazinyl, and 4-(benzoisoxazol-3-yl)piperazinyl.

In the present invention, the $C_1$-$C_6$ alkyl may be linear or branched alkyl. Specifically, the $C_1$-$C_6$ alkyl may be selected from methyl, ethyl, propyl, isopropyl, butyl, isobutyl, t-butyl, hexyl, and isohexyl.

In the present invention, the $C_1$-$C_4$ alkylcarbonyl may be selected from acetyl, propionyl, and butanon-1-yl.

In the present invention, the phenyl substituted with $C_1$-$C_4$ alkyloxy may be selected from the group consisting of methoxyphenyl, ethoxyphenyl, propoxyphenyl, dimethoxyphenyl, diethoxyphenyl, and trimethoxyphenyl.

In the present invention, the pharmaceutically acceptable salt may be prepared using any suitable acid commonly used in the art. Specific examples of such acids include, but are not particularly limited to: non-toxic inorganic acids, such as hydrochloric acid, hydrobromic acid, sulfonic acid, amidosulfuric acid, phosphoric acid, and nitric acid; and non-toxic organic acids, such as acetic acid, propionic acid, succinic acid, glycolic acid, stearic acid, lactic acid, tartaric acid, citric acid, para-toluenesulfonic acid, and methanesulfonic acid.

In the present invention, the carbazole derivative represented by Formula 1 may be selected from compounds represented by Formulae 2 to 5:

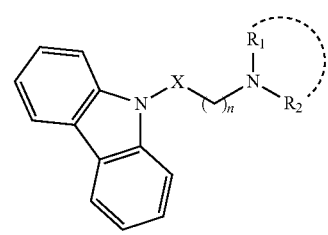

(2)

wherein X, n, $R_1$, and $R_2$ are as defined in Formula 1;

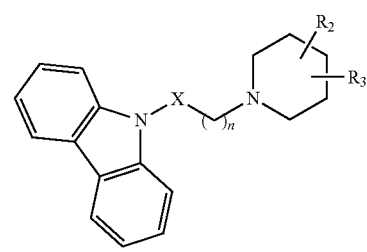

(3)

wherein X, n, $R_2$, and $R_3$ are as defined in Formula 1;

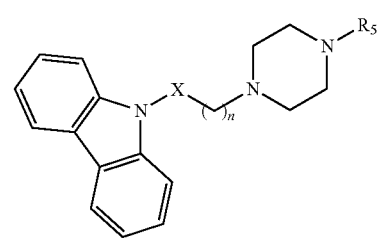

(4)

wherein X, n, and $R_5$ are as defined in Formula 1; and

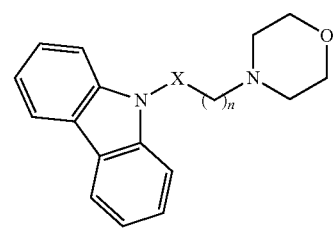

(5)

wherein X and n are as defined in Formula 1.

In Formula 2, the dashed line between $R_1$ and $R_2$ indicates that $R_1$ and $R_2$ may be optionally linked together to form a condensed ring.

In the present invention, the carbazole derivative represented by Formula 1 is particularly preferably selected from the following Compounds 1 to 60:

Compound 1: 6-(Butyl(methyl)amino)-1-(9H-carbazol-9-yl)hexan-1-one

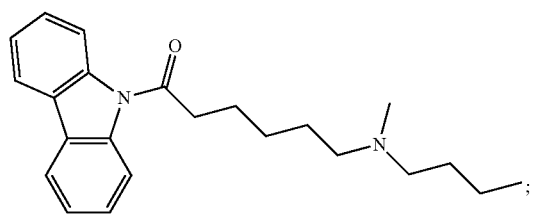 [SMILES: CCCCN(C)CCCCCC(=O)n1c2ccccc2c2ccccc21]

Compound 2: 6-(Benzyl(methyl)amino)-1-(9H-carbazol-9-yl)hexan-1-one

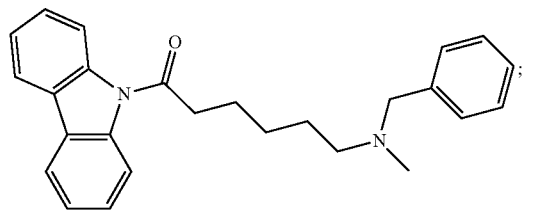 [SMILES: CN(CCCCCC(=O)n1c2ccccc2c2ccccc21)Cc1ccccc1]

Compound 3: 1-(9H-carbazol-9-yl)-6-(pyrrolidin-1-yl)hexan-1-one

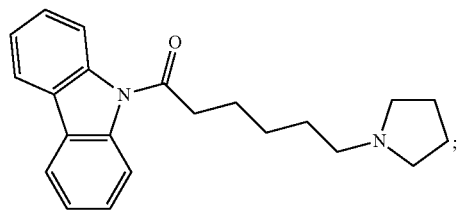 [SMILES: O=C(CCCCCN1CCCC1)n1c2ccccc2c2ccccc21]

Compound 4: 1-(9H-carbazol-9-yl)-6-(4-methylpiperidin-1-yl)hexan-1-one

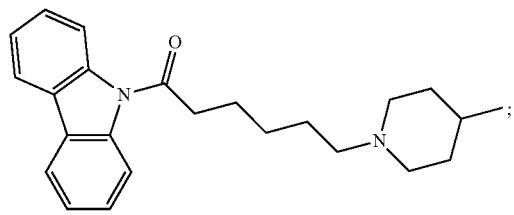 [SMILES: CC1CCN(CCCCCC(=O)n2c3ccccc3c3ccccc32)CC1]

Compound 5: 1-(9H-carbazol-9-yl)-6-(3-methylpiperidin-1-yl)hexan-1-one

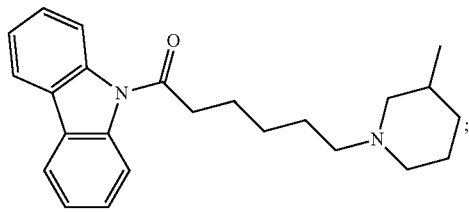 [SMILES: CC1CCCN(CCCCCC(=O)n2c3ccccc3c3ccccc32)C1]

Compound 6: 1-(9H-carbazol-9-yl)-6-(3,5-dimethylpiperidin-1-yl)hexan-1-one

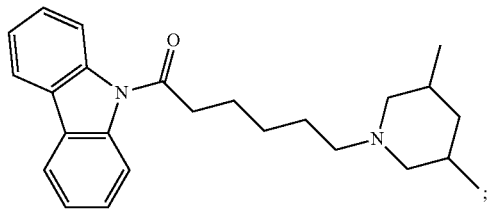 [SMILES: CC1CC(C)CN(CCCCCC(=O)n2c3ccccc3c3ccccc32)C1]

Compound 7: 6-(Azepan-1-yl)-1-(9H-carbazol-9-yl)hexan-1-one

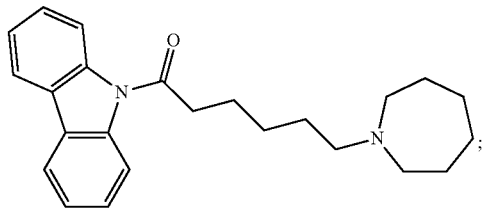 [SMILES: O=C(CCCCCN1CCCCCC1)n1c2ccccc2c2ccccc21]

Compound 8: 1-(9H-carbazol-9-yl)-6-morpholinohexan-1-one

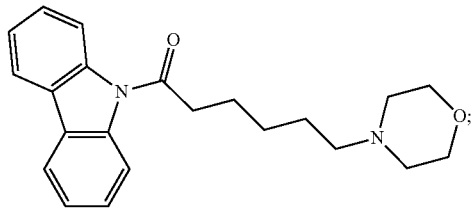 [SMILES: O=C(CCCCCN1CCOCC1)n1c2ccccc2c2ccccc21]

Compound 9: 1-(9H-carbazol-9-yl)-6-(4-phenylpiperidin-1-yl)hexan-1-one

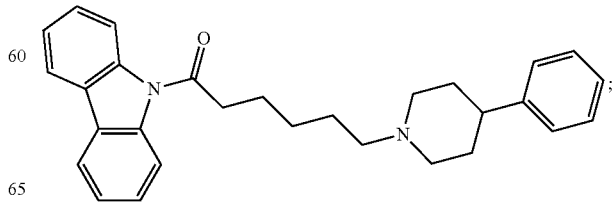

Compound 10: 6-(4-Benzylpiperidin-1-yl)-1-(9H-carbazol-9-yl)hexan-1-one

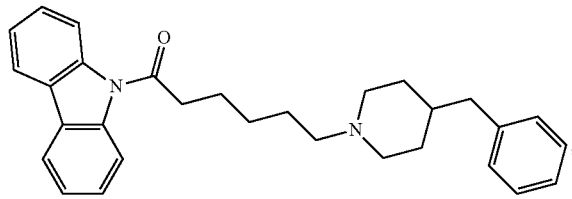

Compound 11: 6-(4-Acetylpiperazin-1-yl)-1-(9H-carbazol-9-yl)hexan-1-one

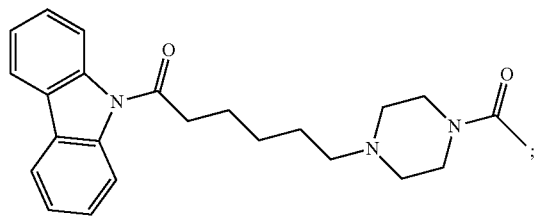 [SMILES: CC(=O)N1CCN(CCCCCC(=O)n2c3ccccc3c3ccccc32)CC1]

Compound 12: 1-(9H-carbazol-9-yl)-6-(4-methylpiperazin-1-yl)hexan-1-one

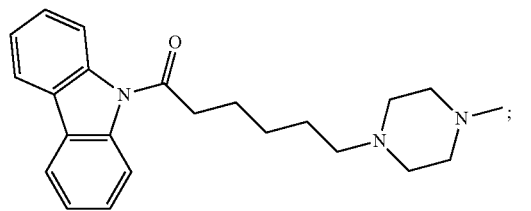 [SMILES: CN1CCN(CCCCCC(=O)n2c3ccccc3c3ccccc32)CC1]

Compound 13: 6-(4-Benzylpiperazin-1-yl)-1-(9H-carbazol-9-yl)hexan-1-one

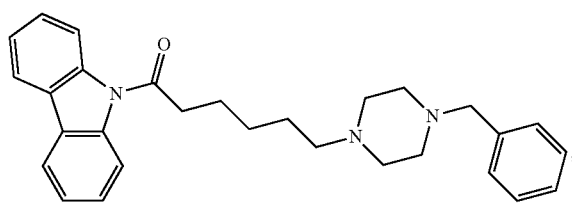

Compound 14: 6-(4-Benzo[d]isoxazol-3-yl)piperazin-1-yl)-1-(9H-carbazol-9-yl)hexan-1-one

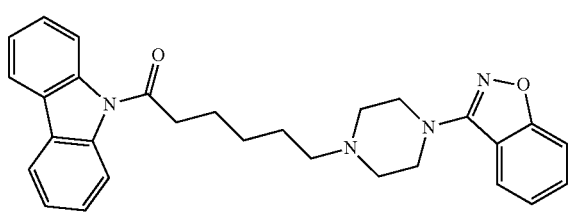

Compound 15: 1-(9H-carbazol-9-yl)-6-(4-(2-hydroxyphenyl)piperazin-1-yl)hexan-1-one

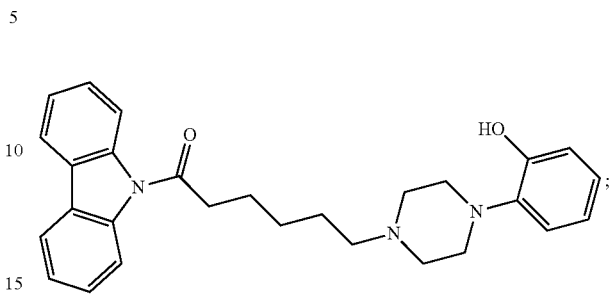

Compound 16: 1-(9H-carbazol-9-yl)-6-(4-(2-methoxyphenyl)piperazin-1-yl)hexan-1-one

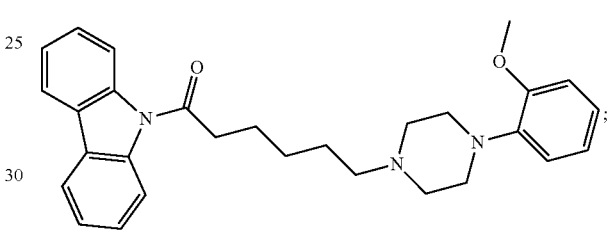

Compound 17: 5-(Butyl(methyl)amino)-1-(9H-carbazol-9-yl)pentan-1-one

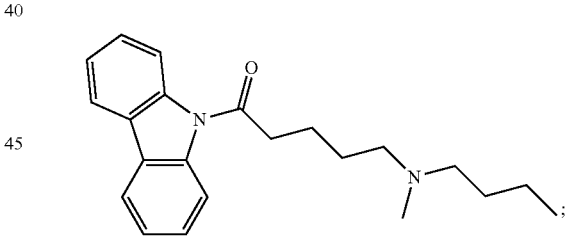

Compound 18: 5-(Benzyl(methyl)amino)-1-(9H-carbazol-9-yl)pentan-1-one

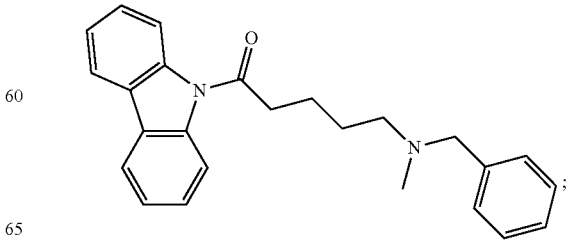

Compound 19: 1-(9H-carbazol-9-yl)-5-(pyrrolidin-1-yl)pentan-1-one

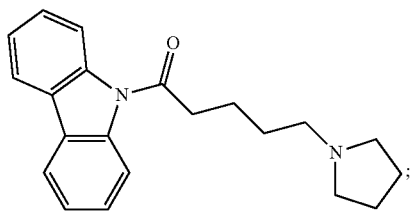 [SMILES: O=C(CCCCN1CCCC1)n1c2ccccc2c2ccccc21]

Compound 20: 1-(9H-carbazol-9-yl)-5-(4-methylpiperidin-1-yl)pentan-1-one

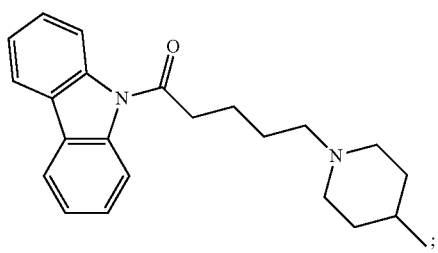 [SMILES: CC1CCN(CCCCC(=O)n2c3ccccc3c3ccccc32)CC1]

Compound 21: 1-(9H-carbazol-9-yl)-5-(3-methylpiperidin-1-yl)pentan-1-one

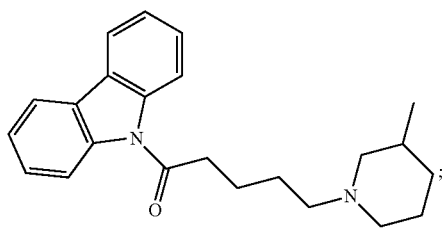 [SMILES: CC1CCCN(CCCCC(=O)n2c3ccccc3c3ccccc32)C1]

Compound 22: 1-(9H-carbazol-9-yl)-5-(3,5-dimethylpiperidin-1-yl)pentan-1-one

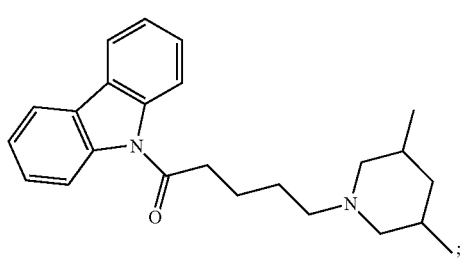 [SMILES: CC1CC(C)CN(CCCCC(=O)n2c3ccccc3c3ccccc32)C1]

Compound 23: 5-(Azepan-1-yl)-1-(9H-carbazol-9-yl)pentan-1-one

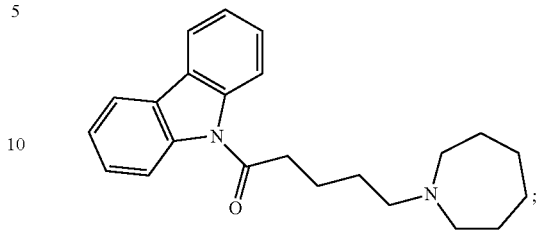

Compound 24: 1-(9H-carbazol-9-yl)-5-morpholinopentan-1-one

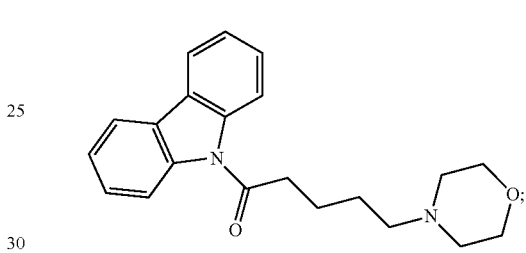

Compound 25: 1-(9H-carbazol-9-yl)-5-(4-phenylpiperidin-1-yl)pentan-1-one

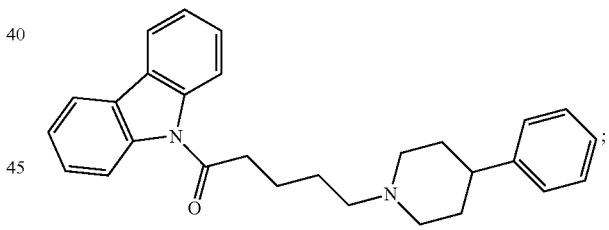

Compound 26: 5-(4-Benzylpiperidin-1-yl)-1-(9H-carbazol-9-yl)pentan-1-one

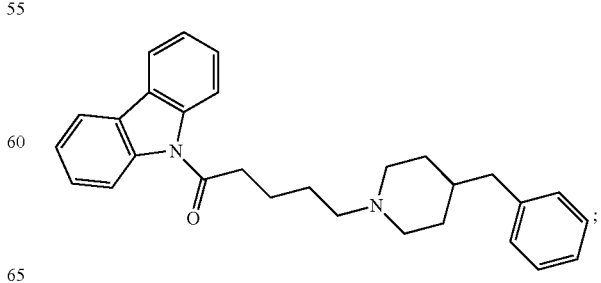

Compound 27: 5-(4-Acetylpiperazin-1-yl)-1-(9H-carbazol-9-yl)pentan-1-one

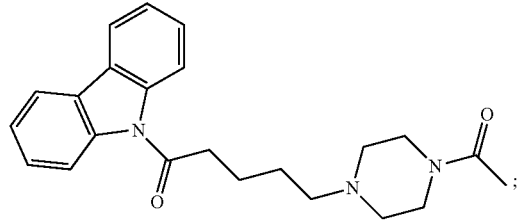 [SMILES: CC(=O)N1CCN(CCCCC(=O)n2c3ccccc3c3ccccc32)CC1]

Compound 28: 1-(9H-carbazol-9-yl)-5-(4-methylpiperazin-1-yl)pentan-1-one

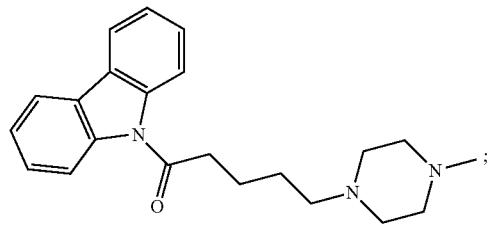 [SMILES: CN1CCN(CCCCC(=O)n2c3ccccc3c3ccccc32)CC1]

Compound 29: 5-(4-Benzylpiperazinyl)-1-(9H-carbazol-9-yl)pentan-1-one

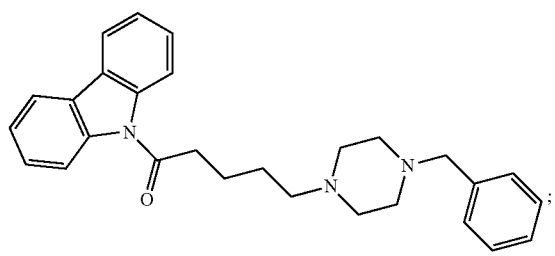 [SMILES: O=C(CCCCN1CCN(Cc2ccccc2)CC1)n1c2ccccc2c2ccccc21]

Compound 30: 1-(9H-carbazol-9-yl)-5-(4-(2-hydroxyphenyl)piperazin-1-yl)pentan-1-one

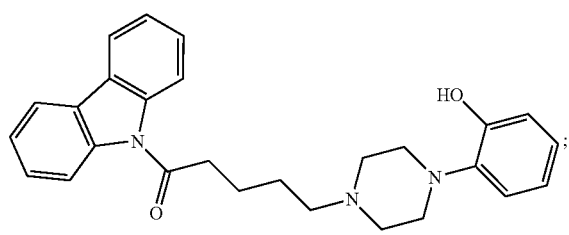 [SMILES: O=C(CCCCN1CCN(c2ccccc2O)CC1)n1c2ccccc2c2ccccc21]

Compound 31: 1-(9H-carbazol-9-yl)-5-(4-(2-methoxyphenyl)piperazin-1-yl)pentan-1-one

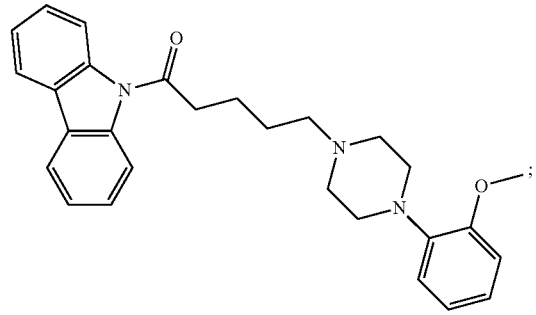 [SMILES: COc1ccccc1N1CCN(CCCCC(=O)n2c3ccccc3c3ccccc32)CC1]

Compound 32: 4-(4-Benzylpiperazin-1-yl)-1-(9H-carbazol-9-yl)butan-1-one

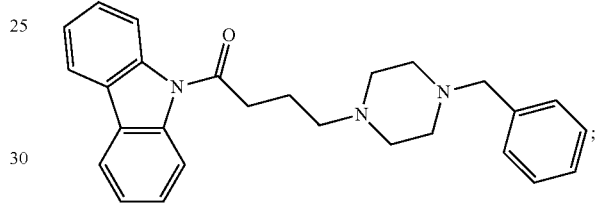

Compound 33: 1-(9H-carbazol-9-yl)-4-(4-(2-hydroxyphenyl)piperazin-1-yl)butan-1-one

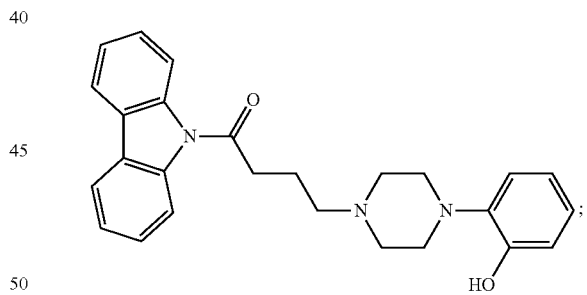

Compound 34: 1-(9H-carbazol-9-yl)-4-(4-(2-methoxyphenyl)piperazin-1-yl)butan-1-one

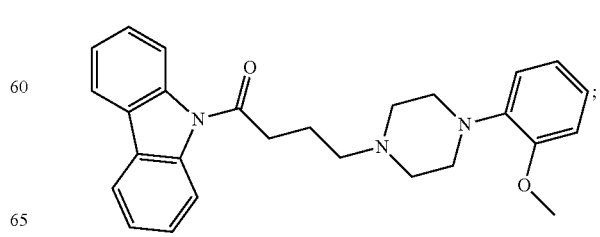

Compound 35: N-butyl-6-(9H-carbazol-9-yl)-N-methyl-hexane-1-amine

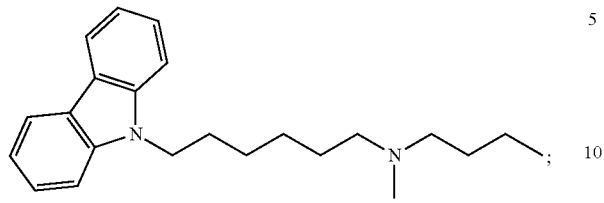

Compound 36: N-benzyl-6-(9H-carbazol-9-yl)-N-methylhexane-1-amine

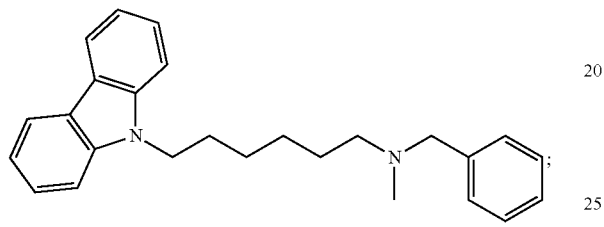

Compound 37: 9-(6-(Pyrrolidin-1-yl)hexyl)-9H-carbazole

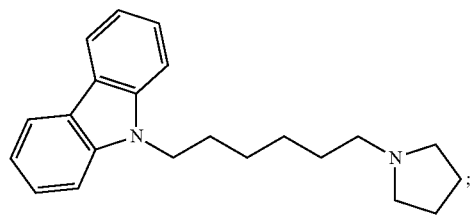 [SMILES: c1ccc2c(c1)c1ccccc1n2CCCCCCN1CCCC1]

Compound 38: 9-(6-(4-Methylpiperidin-1-yl)hexyl)-9H-carbazole

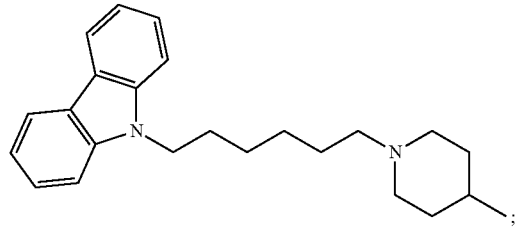

Compound 39: 9-(6-(3-Methylpiperidin-1-yl)hexyl)-9H-carbazole

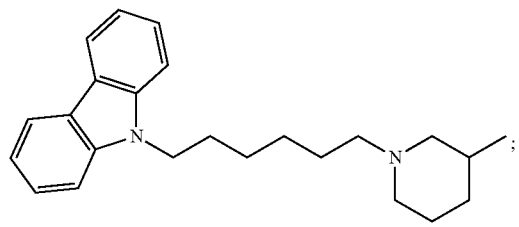 [SMILES: CC1CCCN(CCCCCCn2c3ccccc3c3ccccc32)C1]

Compound 40: 9-(6-(3,5-Dimethylpiperidin-1-yl)hexyl)-9H-carbazole

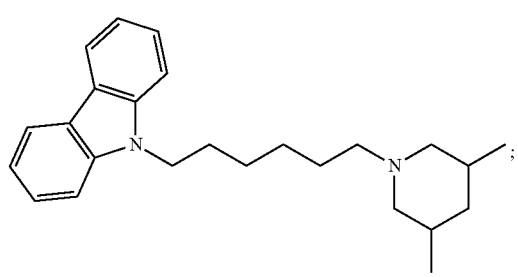 [SMILES: CC1CC(C)CN(CCCCCCn2c3ccccc3c3ccccc32)C1]

Compound 41: 9-(6-(Azepan-1-yl)hexyl)-9H-carbazole

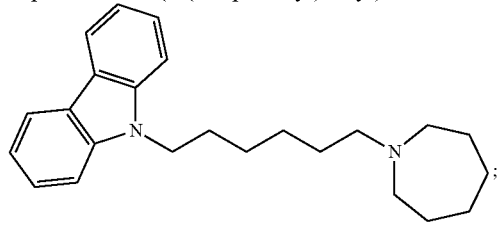 [SMILES: c1ccc2c(c1)c1ccccc1n2CCCCCCN1CCCCCC1]

Compound 42: 4-(6-(9H-carbazol-9-yl)hexyl)morpholine

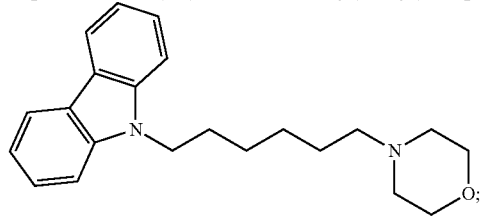 [SMILES: c1ccc2c(c1)c1ccccc1n2CCCCCCN1CCOCC1]

Compound 43: 9-(6-(4-Phenylpiperidin-1-yl)hexyl)-9H-carbazole

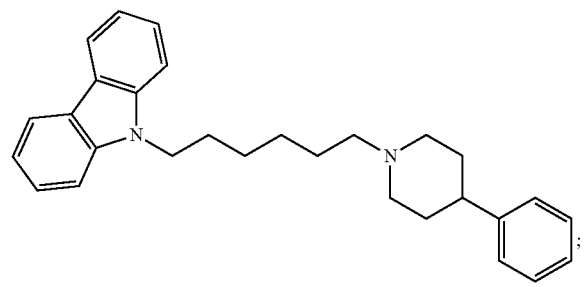 [SMILES: c1ccc(C2CCN(CCCCCCn3c4ccccc4c4ccccc43)CC2)cc1]

Compound 44: 9-(6-(4-Benzylpiperidin-1-yl)hexyl)-9H-carbazole

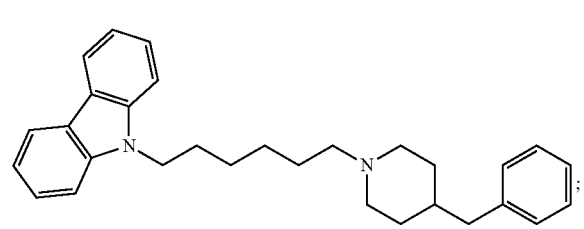 [SMILES: c1ccc(CC2CCN(CCCCCCn3c4ccccc4c4ccccc43)CC2)cc1]

Compound 45: 1-(4-(6-(9H-carbazol-9-yl)hexyl)piperazin-1-yl)ethanone

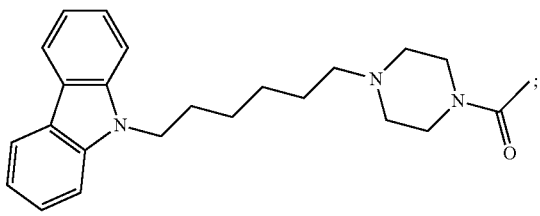 [SMILES: CC(=O)N1CCN(CCCCCCn2c3ccccc3c3ccccc32)CC1]

Compound 46: 9-(6-(4-Methylpiperazin-1-yl)hexyl)-9H-carbazole

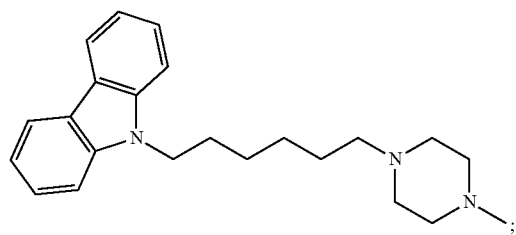

Compound 47: 9-(6-(4-Benzylpiperazin-1-yl)hexyl)-9H-carbazole

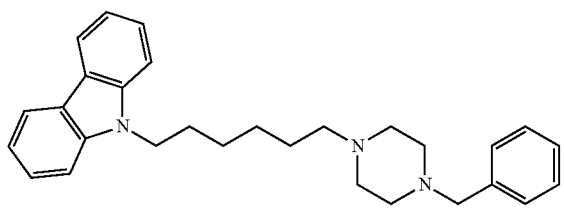

Compound 48: 2-(4-(6-(9H-carbazol-9-yl)hexyl)piperazin-1-yl)phenol

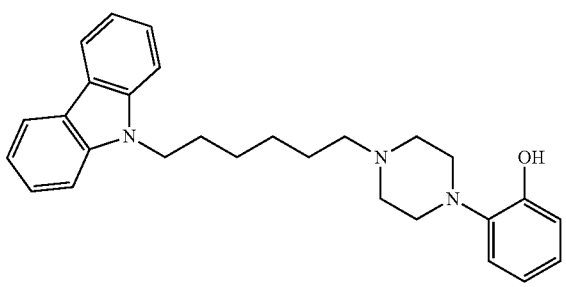

Compound 49: 9-(6-(4-(2-Methoxyphenyl)piperazin-1-yl)hexyl)-9H-carbazole

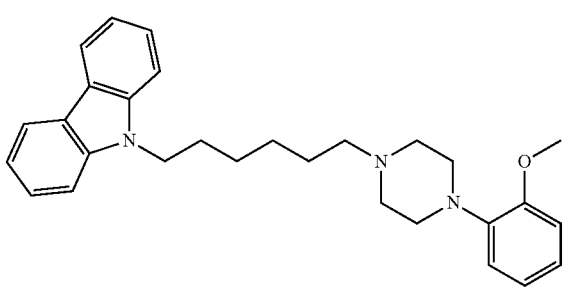

Compound 50: 9-(5-(4-Phenylpiperidin-1-yl)pentyl)-9H-carbazole

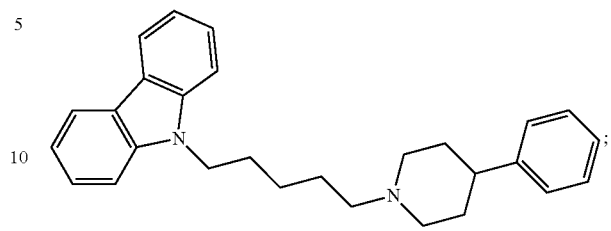

Compound 51: 9-(5-(4-Benzylpiperazin-1-yl)pentyl)-9H-carbazole

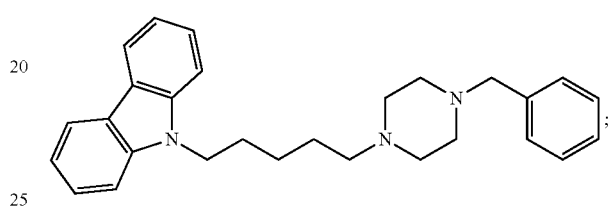

Compound 52: 2-(4-(5-(9H-carbazol-9-yl)pentyl)piperazin-1-yl)phenol

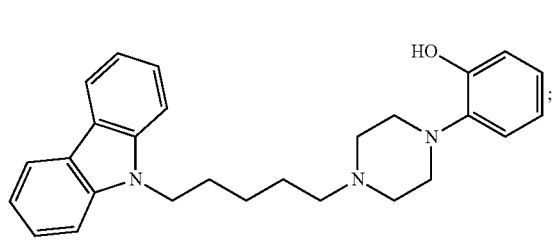 [SMILES: Oc1ccccc1N1CCN(CCCCCn2c3ccccc3c3ccccc32)CC1]

Compound 53: 9-(5-(4-(2-Methoxyphenyl)piperazin-1-yl)pentyl)-9H-carbazole

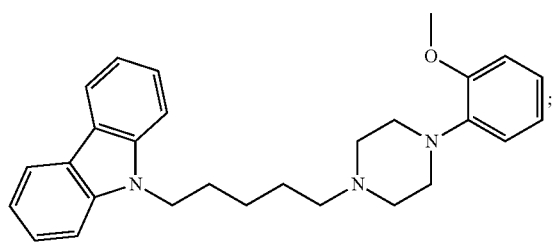 [SMILES: COc1ccccc1N1CCN(CCCCCn2c3ccccc3c3ccccc32)CC1]

Compound 54: 9-(4-(4-Phenylpiperidin-1-yl)butyl)-9H-carbazole

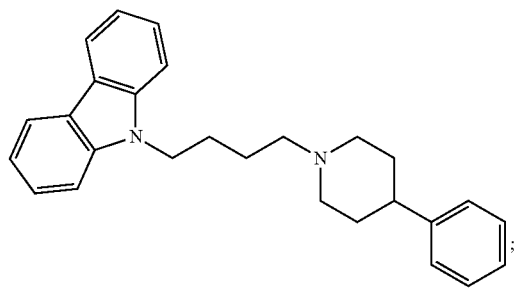 [SMILES: c1ccc(C2CCN(CCCCn3c4ccccc4c4ccccc43)CC2)cc1]

Compound 55: 2-(4-(4-(9H-carbazol-9-yl)butyl)piperazin-1-yl)phenol

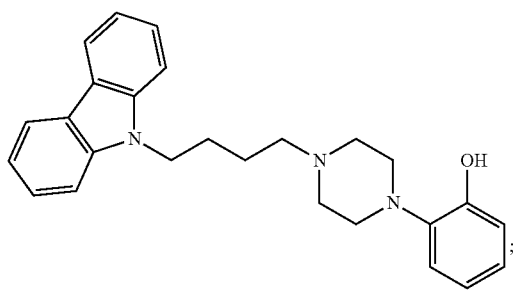 [SMILES: Oc1ccccc1N1CCN(CCCCn2c3ccccc3c3ccccc32)CC1]

Compound 56: 9-(4-(4-(2-Methoxyphenyl)piperazin-1-yl)butyl)-9H-carbazole

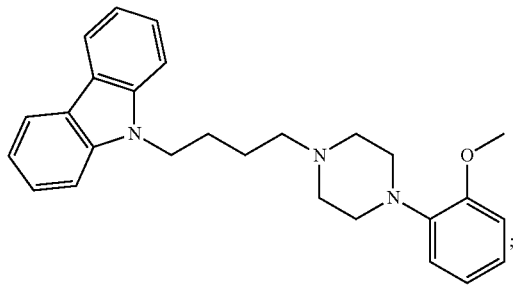 [SMILES: COc1ccccc1N1CCN(CCCCn2c3ccccc3c3ccccc32)CC1]

Compound 57: 9-(3-(4-Phenylpiperidin-1-yl)propyl)-9H-carbazole

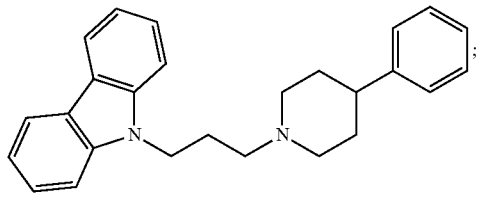 [SMILES: c1ccc(C2CCN(CCCn3c4ccccc4c4ccccc43)CC2)cc1]

Compound 58: 9-(3-(4-Benzylpiperazin-1-yl)propyl)-9H-carbazole

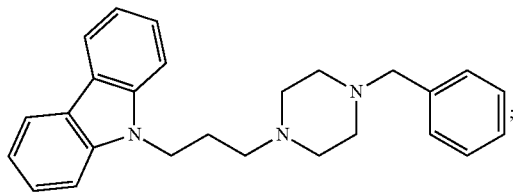 [SMILES: c1ccc(CN2CCN(CCCn3c4ccccc4c4ccccc43)CC2)cc1]

Compound 59: 2-(4-(3-(9H-carbazol-9-yl)propyl)piperazin-1-yl)phenol

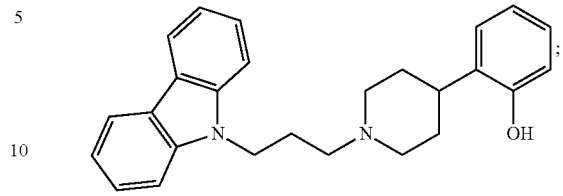

and

Compound 60: 9-(3-(4-(2-Methoxyphenyl)piperazin-1-yl)propyl)-9H-carbazole

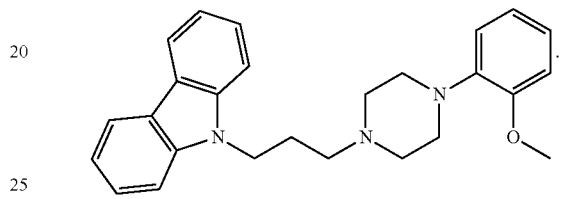

In a further aspect, the present invention provides a method for preparing a carbazole compound represented by Formula 1:

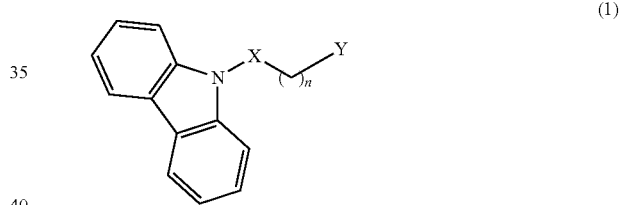

(1)

wherein X, Y, and n are as defined above, the method including reacting a compound represented by Formula 6:

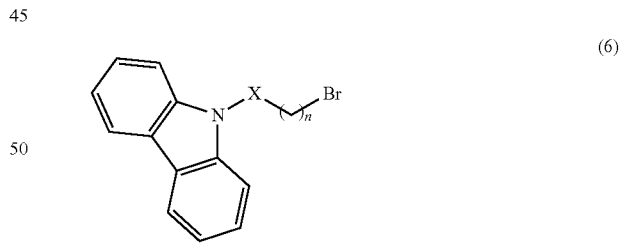

(6)

wherein X and n are as defined above, with a compound represented by Formula 7:

Y—H (7)

wherein Y is as defined above, in an organic solvent.

The organic solvent may be selected from the group consisting of acetonitrile, dichloromethane, dichloroethane, tetrahydrofuran, lower alcohol, N,N-dimethylformamide, dimethyl sulfoxide, ethyl acetate, dioxane, chloroform, benzene, and toluene.

The reaction may be carried out under reflux at 25 to 300° C. for 3 to 24 hours.

The reaction may be carried out in the presence of a base for improved reactivity. The base may be selected from K₂CO₃, triethylamine, and diisopropylethylamine.

In the present invention, the lower alcohol may be methanol, ethanol, propanol or butanol.

According to one embodiment of the present invention, the reaction mixture may be extracted with a suitable organic solvent known in the art. Specifically, the reaction mixture is diluted with an organic solvent selected from dichloromethane, diethyl ether, and ethyl acetate, a weakly acidic aqueous solution is added thereto, the organic layer is separated from the aqueous layer, the remaining water molecules are removed from the organic layer, followed by concentration and purification.

The purification may be performed by any suitable technique known in the art, preferably column chromatography on silica gel, to obtain the desired carbazole derivative represented by Formula 1.

The pharmaceutically acceptable salt of the carbazole derivative represented by Formula 1 may be prepared using a non-toxic inorganic or organic acid. Examples of suitable non-toxic inorganic acids include hydrochloric acid, hydrobromic acid, sulfonic acid, amidosulfuric acid, phosphoric acid, and nitric acid. Examples of suitable non-toxic organic acids include acetic acid, propionic acid, succinic acid, glycolic acid, stearic acid, lactic acid, tartaric acid, citric acid, para-toluenesulfonic acid, and methanesulfonic acid.

According to one embodiment of the present invention, the compound of Formula 6 may be prepared by reacting carbazole with a compound of Formula 8:

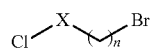

(8)

wherein X and n are as defined above, in an organic solvent.

The organic solvent may be selected from the group consisting of acetonitrile, dichloromethane, dichloroethane, tetrahydrofuran, lower alcohol, N,N-dimethylformamide, dimethyl sulfoxide, ethyl acetate, dioxane, chloroform, benzene, and toluene.

The reaction may be carried out under reflux at 25 to 200° C. for 3 to 24 hours. The desired compound may be obtained by any suitable purification technique known in the art. Preferably, the carbazole compound of Formula 6 is purified by column chromatography on silica gel.

According to one embodiment of the present invention, when X in Formula 8 is CH₂, the reaction for the preparation of the compound of Formula 6 may be carried out in the presence of a base. The base may be selected from t-BuOK, triethylamine, and diisopropylethylamine. When X is C(O), the reaction for the preparation of the compound of Formula 6 is preferably carried out in the dark, where improved reactivity is ensured and side reactions are prevented.

In another aspect, the present invention provides a pharmaceutical composition for preventing and treating a central nervous system disease, including the carbazole compound represented by Formula 1 or pharmaceutically acceptable salt thereof as an active ingredient.

The central nervous system disease may be selected from the group consisting of depression, migraine, anxiety, pain, inflammatory pain, neuropathic pain, body temperature dysregulation, circadian rhythm dysregulation, sleep disturbance, smooth muscle-related diseases, and combinations thereof.

The pharmaceutical composition of the present invention has a binding affinity for the 5-HT₇ receptor and exhibits an inhibitory activity against the 5-HT₇ receptor due to its selective antagonism against the 5-HT₇ receptor.

According to one embodiment of the present invention, the carbazole compound or pharmaceutically acceptable salt thereof may be mixed with a carrier, excipient or diluent known in the art and the mixture may be formulated into a dosage form suitable for oral or parenteral administration by any suitable technique known in the art.

Examples of such carriers, excipients or diluents include lactose, dextrose, sucrose, sorbitol, mannitol, xylitol, erythritol, maltitol, starch, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, and mineral oil.

For formulation, the pharmaceutical composition may further include at least one additive selected from fillers, extenders, binders, wetting agents, disintegrants, and surfactants known in the art. A lubricating agent such as magnesium stearate or talc may be further added during formulation.

For oral administration, the pharmaceutical composition may be in the form of tablets, capsules, solutions, suspensions, and the like. For parenteral administration, the pharmaceutical composition may be in the form of preparations for intraperitoneal, subcutaneous, intramuscular, and transdermal injections.

According to one embodiment of the present invention, the pharmaceutical composition is a 5-HT₇ serotonin receptor modulator. The pharmaceutical composition is administered in an amount such that the effective dose of the carbazole derivative of Formula 1 or pharmaceutically acceptable salt thereof ranges from 0.01 to 1000 mg/day for an adult. The daily dose may depend on the age, weight, sex, and general health of the patient, the mode of administration, and the severity of diseases to be treated. The daily dose may be administered in a single dose or in divided doses at regular time intervals according to the judgment of the physician or pharmacist.

Thus, the present invention provides the medical use of the carbazole compound represented by Formula 1 or pharmaceutically acceptable salt thereof or the pharmaceutical composition for the prevention and treatment of diseases.

Specifically, the present invention includes the medical use of the carbazole compound represented by Formula 1 or pharmaceutically acceptable salt thereof or the pharmaceutical composition, which acts as a 5-HT₇ serotonin receptor modulator, for the prevention and treatment of neurological diseases, such as depression, migraine, anxiety, and pain, particularly inflammatory pain and neuropathic pain, body temperature dysregulation, circadian rhythm dysregulation, sleep disturbance, and smooth muscle-related diseases.

The present invention will be explained in more detail with reference to the following examples. However, it will be obvious to those skilled in the art that these examples are provided for illustrative purposes only and are not intended to limit the scope of the invention.

EXAMPLES

Example 1.1:
6-Bromo-1-(9H-carbazol-9-yl)hexan-1-one

Carbazole (2 g, 11.96 mmol) was dissolved in toluene (100 ml) in the reactor, which was covered with a foil to prevent light from entering. To the solution was added 6-bromohexanoyl chloride (5.1 g, 23.92 mmol). The mixture was heated to reflux at 115° C. for 18 h. After completion of the reaction, the reaction solution was concentrated under reduced pressure and diluted with $CH_2C_{12}$. The diluted solution was washed with 1 N HCl and $H_2O$, dried over anhydrous $Na_2SO_4$, and filtered. The filtrate was concentrated under reduced pressure. The resulting concentrate was purified by silica gel column chromatography (hexane:EtOAc=20:1), giving 3.4 g (9.88 mmol, 83% yield) of the title compound.

$^1$H NMR (400 MHz, $CDCl_3$) δ 7.77 (dd, J=7.7 Hz, J=1.2 Hz, 1H), 7.64 (td, J=7.7 Hz, J=1.2 Hz, 1H), 7.58-7.42 (m, 7H)

Example 1.2: 5-Bromo-1-(9H-carbazol-9-yl)pentan-1-one

The title compound was prepared in the same manner as in Example 1.1, except that 5-bromopentanoyl chloride was used instead of 6-bromohexanoyl chloride.

Example 1.3: 4-Bromo-1-(9H-carbazol-9-yl)butan-1-one

The title compound was prepared in the same manner as in Example 1.1, except that 4-bromobutanoyl chloride was used instead of 6-bromohexanoyl chloride.

Example 1.4: 9-(6-Bromohexyl)-9H-carbazole

Carbazole (2 g, 11.96 mmol), 1,6-dibromohexane (2.8 ml, 17.94 mmol), and t-BuOK (1.3 g, 11.96 mmol) were dissolved in THF (15 ml) in a reactor. The solution was stirred under heating at 40° C. for 10 h. After completion of the reaction, the reaction solution was concentrated under reduced pressure and diluted with $CH_2C_{12}$. The diluted solution was washed with $H_2O$, dried over anhydrous $Na_2SO_4$, and filtered. The filtrate was concentrated under reduced pressure. The concentrate was purified by silica gel column chromatography (hexane:MC=8:1), giving 2.1 g (6.36 mmol, 53% yield) of the title compound.

$^1$H NMR (400 MHz, $CDCl_3$) δ 8.03-8.01 (m, 2H), 7.39-7.35 (m, 2H), 7.25 (d, J=8.2 Hz, 2H), 7.15 (td, J=7.4 Hz, J=0.8 Hz, 2H), 4.07 (t, J=7.1 Hz, 2H), 3.17 (t, J=6.7 Hz, 2H), 1.72-1.57 (m, 4H), 1.30-1.14 (m, 4H)

Example 1.5: 9-(5-Bromopentyl)-9H-carbazole

The title compound was prepared in the same manner as in Example 1.4, except that 1,5-dibromopentane was used instead of 1,6-dibromohexane.

Example 1.6: 9-(4-Bromobutyl)-9H-carbazole

The title compound was prepared in the same manner as in Example 1.4, except that 1,4-dibromobutane was used instead of 1,6-dibromohexane.

Example 1.7: 9-(3-Bromopropyl)-9H-carbazole

The title compound was prepared in the same manner as in Example 1.4, except that 1,3-dibromopropane was used instead of 1,6-dibromohexane.

Example 2

Example 2.1: 6-(Butyl(methyl)amino)-1-(9H-carbazol-9-yl)hexan-1-one hydrochloride The compound of Example 1.1 (100 mg, 0.29 mmol) and N-methylbutylamine (0.02 ml, 0.35 mmol) were dissolved in acetonitrile (10 ml) in a reactor. The solution was heated to reflux at 85° C. for 21 h. After completion of the reaction, the reaction mixture was diluted with $CH_2C_{12}$, and 0.5 N HCl and $H_2O$ were then added thereto. The aqueous layer was extracted with $CH_2C_{12}$. The obtained organic layer was dried over anhydrous $Na_2SO_4$ and filtered. The filtrate was concentrated under reduced pressure. The concentrate was purified by silica gel column chromatography (MC:MeOH=20:1). The crude product was added dropwise to a solution of 0.5 N hydrochloric acid (0.30 ml, 0.34 mmol) in dimethyl ether to obtain a solid precipitate. Filtration of the precipitate gave 64.4 mg (0.17 mmol, 57% yield) of the title compound.

$^1$H NMR (400 MHz, $CDCl_3$) δ 11.57 (brs, 0.8H), 8.21 (d, J=8.4 Hz, 2H), 7.99 (dd, J=5.7 Hz, J=0.9 Hz, 2H), 7.48 (td, J=7.8 Hz, J=1.2 Hz, 2H), 7.38 (t, J=7.2 Hz, 2H), 3.19 (t, J=6.7 Hz, 2H), 3.11-2.90 (m, 4H), 2.76 (d, J=4.6 Hz, 3H), 2.04-1.77 (m, 6H), 1.63-1.58 (m, 2H), 1.45-1.36 (m, 2H), 0.97 (t, J=7.3 Hz, 3H)

Example 2.2: 6-(Benzyl)methyl)amino)-1-(9H-carbazol-9-yl)hexan-1-one hydrochloride 70.0 mg (0.17 mmol, 57% yield) of the title compound was prepared using the compound of Example 1.1 (100 mg, 0.29 mmol) and N-benzylmethylamine (0.04 ml, 0.35 mmol) in accordance with the procedure of Example 2.1.

$^1$H NMR (400 MHz, $CDCl_3$) δ 12.08 (brs, 0.8H), 8.22 (d, J=8.4 Hz, 2H), 8.00 (dd, J=5.7 Hz, J=0.9 Hz, 2H), 7.61-7.59 (m, 2H), 7.51-7.38 (m, 7H), 4.18 (brd, J=12.6 Hz, 2H), 3.18 (t, J=6.7 Hz, 2H), 3.12 (brs, 1H), 2.89 (brs, 1H), 2.69 (s, 3H), 2.12 (brs, 1H), 1.97 (quint, J=7.1 Hz, 3H), 1.58 (brs, 2H)

Example 2.3: 1-(9H-carbazol-9-yl)-6-(pyrrolidin-1-yl)hexan-1-one hydrochloride 98.0 mg (0.26 mmol, 91% yield) of the title compound was prepared using the compound of Example 1.1 (100 mg, 0.29 mmol) and pyrrolidine (0.03 ml, 0.35 mmol) in accordance with the procedure of Example 2.1.

$^1$H NMR (300 MHz, $CDCl_3$) δ 11.85 (brs, 0.8H), 8.22 (d, J=8.2 Hz, 2H), 8.00 (d, J=7.2 Hz, 2H), 7.49 (t, J=7.4 Hz, 2H), 7.39 (t, J=7.4 Hz, 2H), 3.82 (brs, 2H), 3.19 (t, J=6.3 Hz, 2H), 3.09 (brs, 2H), 2.79 (brs, 2H), 2.26 (brs, 2H), 2.06-1.99 (m, 6H), 1.64 (s, 2H)

Example 2.4: 1-(9H-carbazol-9-yl)-6-(4-methylpiperidin-1-yl)hexan-1-one

The compound of Example 1.1 (100 mg, 0.29 mmol) and 4-methylpiperidine (0.04 ml, 0.35 mmol) were dissolved in acetonitrile (10 ml) in a reactor. The solution was heated to reflux at 85° C. for 21 h. After completion of the reaction, the reaction mixture was diluted with $CH_2C_{12}$, and 0.5 N HCl and $H_2O$ were then added thereto. The aqueous layer was extracted with $CH_2C_{12}$. The obtained organic layer was dried over anhydrous $Na_2SO_4$ and filtered. The filtrate was concentrated under reduced pressure. The concentrate was purified by silica gel column chromatography (hexane:EtOAc=4:1), giving 51 mg (0.14 mmol, 48% yield) of the final title compound.

$^1$H NMR (300 MHz, CDCl$_3$) δ 8.22 (d, J=8.3 Hz, 2H), 8.02-7.99 (m, 2H), 7.51-7.45 (m, 2H), 7.38 (td, J=7.5 Hz, J=0.9 Hz, 2H), 3.16 (t, J=7.4 Hz, 2H), 2.91 (brd, J=11.7 Hz, 2H), 2.36 (t, J=7.6 Hz, 2H), 2.04-1.83 (m, 4H), 1.67-1.47 (m, 6H), 1.38-1.19 (m, 3H), 0.92 (d, J=6.0 Hz, 3H)

Example 2.5: 1-(9H-carbazol-9-yl)-6-(3-methylpiperidin-1-yl)hexan-1-one hydrochloride 63.6 mg (0.16 mmol, 55% yield) of the title compound was prepared using the compound of Example 1.1 (100 mg, 0.29 mmol) and 3-methylpiperidine (0.04 ml, 0.35 mmol) in accordance with the procedure of Example 2.1.

$^1$H NMR (400 MHz, CDCl$_3$) δ 11.22 (brs, 0.8H), 8.23 (d, J=8.4 Hz, 2H), 8.01 (dd, J=5.7 Hz, J=0.9 Hz, 2H), 7.52-7.47 (m, 2H), 7.39 (t, J=7.3 Hz, 2H), 3.57 (brd, J=10.2 Hz, 1H), 3.49-3.43 (m, 1H), 3.20 (t, J=6.7 Hz, 2H), 2.98-2.97 (m, 2H), 2.54-2.37 (m, 3H), 2.21 (q, J=10.9 Hz, 1H), 2.08-1.85 (m, 7H), 1.59 (s, 1H), 1.14-1.04 (m, 1H), 0.96 (d, J=6.6 Hz, 3H)

Example 2.6: 1-(9H-carbazol-9-yl)-6-(3,5-dimethylpiperidin-1-yl)hexan-1-one hydrochloride 82.5 mg (0.20 mmol, 69% yield) of the title compound was prepared using the compound of Example 1.1 (100 mg, 0.29 mmol) and 3,5-dimethylpiperidine (0.05 ml, 0.35 mmol) in accordance with the procedure of Example 2.1.

$^1$H NMR (400 MHz, CDCl$_3$) δ 11.64 (brs, 0.8H) 8.22 (d, J=8.3 Hz, 2H), 8.00 (d, J=7.6 Hz, 2H), 7.49 (t, J=7.4 Hz, 2H), 7.39 (t, J=7.4 Hz, 2H), 3.40 (brd, J=9.2 Hz, 2H), 3.19 (t, J=6.2 Hz, 2H), 2.96 (brs, 2H), 2.52 (brs, 2H), 2.16-1.90 (m, 7H), 1.58 (brs, 3H), 0.95 (d, J=6.3 Hz, 6H);

Example 2.7: 6-(Azepan-1-yl)-1-(9H-carbazol-9-yl)hexan-1-one hydrochloride 95.7 mg (0.24 mmol, 83% yield) of the title compound was prepared using the compound of Example 1.1 (100 mg, 0.29 mmol) and hexamethyleneimine (0.04 ml, 0.35 mmol) in accordance with the procedure of Example 2.1.

$^1$H NMR (300 MHz, CDCl$_3$) δ 11.53 (brs, 0.8H), 8.22 (d, J=8.3 Hz, 2H), 8.00 (d, J=7.6 Hz, 2H), 7.49 (t, J=7.8 Hz, 2H), 7.39 (t, J=7.4 Hz, 2H), 3.56-3.54 (m, 2H), 3.19 (t, J=6.7 Hz, 2H), 3.03-2.88 (m, 4H), 2.22-2.15 (m, 2H), 2.04-1.94 (m, 4H), 1.87-1.81 (m, 4H), 1.61 (s, 4H)

Example 2.8: 1-(9H-carbazol-9-yl)-6-morpholinohexan-1-one hydrochloride 31.6 mg (0.08 mmol, 28% yield) of the title compound was prepared using the compound of Example 1.1 (100 mg, 0.29 mmol) and morpholine (0.03 ml, 0.35 mmol) in accordance with the procedure of Example 2.1.

$^1$H NMR (400 MHz, CDCl$_3$) δ 12.75 (brs, 0.8H), 8.22 (brd, J=6.7 Hz, 2H), 8.00 (d, J=7.6 Hz, 2H), 7.49 (brs, 2H), 7.39 (t, J=7.2 Hz, 2H), 4.36 (brs, 2H), 3.99 (brs, 2H), 3.49-3.45 (m, 2H), 3.20 (brs, 2H), 3.04 (brs, 2H), 2.88 (brs, 2H), 2.05 (brd, J=30.7 Hz, 4H), 1.60 (s, 2H)

Example 2.9: 1-(9H-carbazol-9-yl)-6-(4-phenylpiperidin-1-yl)hexan-1-one hydrochloride 45.6 mg (0.10 mmol, 34% yield) of the title compound was prepared using the compound of Example 1.1 (100 mg, 0.29 mmol) and 4-phenylpiperidine (56 mg, 0.35 mmol) in accordance with the procedure of Example 2.1.

$^1$H NMR (400 MHz, CDCl$_3$) δ 11.95 (brs, 0.8H), 8.23 (d, J=8.4 Hz, 2H), 8.01 (dd, J=5.7 Hz, J=0.8 Hz, 2H), 7.52-7.48 (m, 2H), 7.40 (t, J=7.5 Hz, 2H), 7.34-7.23 (m, 5H), 3.70 (brd, J=10.2 Hz, 2H), 3.21 (t, J=6.7 Hz, 2H), 3.04 (brs, 2H), 2.80-2.65 (m, 4H), 2.11 (brs, 3H), 2.02 (brd, J=11.0 Hz, 3H), 1.63-1.58 (m, 3H)

Example 2.10: 6-(4-Benzylpiperidin-1-yl)-1-(9H-carbazol-9-yl)hexan-1-one hydrochloride 88.4 mg (0.19 mmol, 64% yield) of the title compound was prepared using the compound of Example 1.1 (100 mg, 0.29 mmol) and 4-benzylpiperidine (0.06 ml, 0.35 mmol) in accordance with the procedure of Example 2.1.

$^1$H NMR (400 MHz, CDCl$_3$) δ 11.51 (brs, 0.8H), 8.22 (brs, 2H), 7.99 (brd, J=6.6 Hz, 2H), 7.49 (brs, 2H), 7.38 (brs, 2H), 7.29 (brs, 2H), 7.22 (brs, 1H), 7.14 (brs, 2H), 3.66 (brs, 2H), 3.19 (brs, 2H), 3.03 (brs, 2H), 2.64 (s, 4H), 2.10 (brd, J=59.6 Hz, 6H), 1.85 (brs, 3H), 1.71 (s, 2H)

Example 2.11: 6-(4-Acetylpiperazin-1-yl)-1-(9H-carbazol-9-yl)hexan-1-one hydrochloride 55.4 mg (0.13 mmol, 45% yield) of the title compound was prepared using the compound of Example 1.1 (100 mg, 0.29 mmol) and acetylpiperazine (45 mg, 0.35 mmol) in accordance with the procedure of Example 2.1.

$^1$H NMR (400 MHz, MeOD) δ 8.24 (brs, 2H), 8.05 (brs, 2H), 7.47 (brs, 2H), 7.38 (brd, J=3.3 Hz, 2H), 4.64 (brd, J=12.9 Hz, 1H), 4.12 (brs, 1H), 3.59 (brs, 4H), 3.24-2.99 (m, 4H), 2.15 (s, 3H), 1.92 (brd, J=32.3 Hz, 5H), 1.59 (brs, 3H)

Example 2.12: 1-(9H-carbazol-9-yl)-6-(4-methylpiperazin-1-yl)hexan-1-one hydrochloride 83.8 mg (0.21 mmol, 72% yield) of the title compound was prepared using the compound of Example 1.1 (100 mg, 0.29 mmol) and methylpiperazine (0.03 ml, 0.35 mmol) in accordance with the procedure of Example 2.1.

$^1$H NMR (400 MHz, MeOD) δ 8.26 (d, J=8.4 Hz, 2H), 8.07 (d, J=7.6 Hz, 2H), 7.51-7.47 (m, 2H), 7.39 (t, J=7.4 Hz, 2H), 3.48-3.24 (m, 10H), 2.99 (brs, 2H), 2.78 (s, 3H), 1.96 (quint, J=7.3 Hz, 2H), 1.79 (brs, 2H), 1.58 (quint, J=7.5 Hz, 2H)

Example 2.13: 6-(4-Benzylpiperazin-1-yl)-1-(9H-carbazol-9-yl)hexan-1-one hydrochloride 135.0 mg (0.28 mmol, 98% yield) of the title compound was prepared using the compound of Example 1.1 (100 mg, 0.29 mmol) and benzylpiperazine (0.06 ml, 0.35 mmol) in accordance with the procedure of Example 2.1.

$^1$H NMR (400 MHz, DMSO) δ 11.48 (brs, 0.8H), 8.27 (d, J=8.4 Hz, 2H), 8.19 (dd, J=5.7 Hz, J=0.7 Hz, 2H), 7.60 (brs, 2H), 7.54-7.49 (m, 2H), 7.45-7.40 (m, 5H), 4.32 (brs, 2H), 3.66 (brs, 2H), 3.42 (s, 4H), 3.27 (t, J=7.0 Hz, 4H), 3.11 (brs, 2H), 1.83-1.77 (m, 4H), 1.49-1.47 (m, 2H)

Example 2.14: 6-(4-Benzo[d]isoxazol-3-yl)piperazin-1-yl)-1-(9H-carbazol-9-yl)hexan-1-one hydrochloride 6.3 mg (0.01 mmol, 4% yield) of the title compound was prepared using the compound of Example 1.1 (100 mg, 0.29 mmol) and 3-(1-piperazinyl)-1,2-benzisoxazole (71 mg, 0.35 mmol) in accordance with the procedure of Example 2.1.

$^1$H NMR (400 MHz, CDCl$_3$) δ 13.21 (brs, 0.8H), 8.20 (brd, J=6.4 Hz, 2H), 7.99 (d, J=7.5 Hz, 2H), 7.61 (brs, 2H), 7.55-7.48 (m, 4H), 7.38 (t, J=7.1 Hz, 2H), 4.15 (brs, 4H), 3.56 (brs, 2H), 3.19 (brs, 2H), 3.05 (brs, 5H), 2.08-1.99 (m, 5H)

Example 2.15: 1-(9H-carbazol-9-yl)-6-(4-(2-hydroxyphenyl)piperazin-1-yl)hexan-1-one 195 mg (0.44 mmol, 76% yield) of the title compound was prepared using 1-(2-hydroxyphenyl)piperazine (124 mg, 0.70 mmol), the compound of Example 1.1 (200 mg, 0.58 mmol), and K$_2$CO$_3$ (80 mg, 0.58 mmol) in accordance with the procedure of Example 2.4.

$^1$H NMR (300 MHz, CDCl$_3$) δ 8.24 (d, J=9.0 Hz, 2H), 8.02 (dd, J=7.6, 0.7 Hz, 2H), 7.49 (td, J=7.8, 1.4 Hz, 2H), 7.40 (td, J=7.4, 0.8 Hz, 2H), 7.17 (dd, J=7.8, 1.2 Hz, 1H), 7.10-7.05 (m, 1H), 6.95 (dd, J=8.1, 1.5 Hz, 1H), 6.88-6.83 (m, 1H), 3.19 (t, J=7.4 Hz, 2H), 2.91 (brt, J=4.5 Hz, 4H), 2.63 (brs, 4H), 2.47 (t, J=7.2 Hz, 2H), 2.05-1.94 (m, 2H), 1.66-1.53 (m, 4H)

Example 2.16: 1-(9H-carbazol-9-yl)-6-(4-(2-methoxyphenyl)piperazin-1-yl)hexan-1-one 21 mg (0.046 mmol, 77% yield) of the title compound was prepared using 1-(2-methoxyphenyl)piperazine (13.4 mg, 0.07 mmol), the compound of Example 1.1 (20 mg, 0.06 mmol), and K$_2$CO$_3$ (8 mg, 0.06 mmol) in accordance with the procedure of Example 2.4.

$^1$H NMR (300 MHz, CDCl$_3$) δ 8.22 (d, J=8.4 Hz, 2H), 7.99 (dt, J=7.6, 0.7 Hz, 2H), 7.50-7.45 (m, 2H), 7.38 (td, J=7.4, 1.0 Hz, 2H), 7.02-6.92 (m, 4H), 3.86 (s, 3H), 3.17-3.12 (m, 6H), 2.66 (brs, 4H), 2.46 (t, J=7.5 Hz, 2H), 2.02-1.92 (m, 2H), 1.68-1.51 (m, 4H)

Example 2.17: 5-(Butyl(methyl)amino)-1-(9H-carbazol-9-yl)pentan-1-one hydrochloride 82.0 mg (0.22 mmol, 73% yield) of the title compound was prepared using the compound of Example 1.2 (100 mg, 0.30 mmol) and N-methylbutylamine (0.04 ml, 0.36 mmol) in accordance with the procedure of Example 2.1.

$^1$H NMR (400 MHz, CDCl$_3$) δ 11.41 (brs, 0.8H), 8.19 (d, J=8.3 Hz, 2H), 7.99 (d, J=7.5 Hz, 2H), 7.47 (t, J=7.5 Hz, 2H), 7.38 (t, J=7.5 Hz, 2H), 3.25 (t, J=6.0 Hz, 2H), 3.17-3.06 (m, 5H), 2.77 (s, 3H), 2.12 (brs, 2H), 2.02-2.00 (m, 2H), 1.90 (brs, 1H), 1.80 (brs, 1H), 1.40 (brd, J=6.7 Hz, 2H), 0.97 (t, J=7.3 Hz, 3H)

Example 2.18: 5-(Benzyl(methyl)amino)-1-(9H-carbazol-9-yl)pentan-1-one hydrochloride 90.7 mg (0.22 mmol, 74% yield) of the title compound was prepared using the compound of Example 1.2 (100 mg, 0.30 mmol) and N-benzylmethylamine (0.05 ml, 0.36 mmol) in accordance with the procedure of Example 2.1.

$^1$H NMR (400 MHz, CDCl$_3$) δ 12.72 (brs, 0.8H), 8.20 (d, J=8.2 Hz, 2H), 8.01 (dd, J=5.7 Hz, 0.8 Hz, 2H), 7.62 (brd, J=3.4 Hz, 2H), 7.51-7.38 (m, 7H), 4.20 (q, J=14.0 Hz, 2H), 3.23-3.17 (m, 3H), 2.93 (brs, 1H), 2.72 (s, 3H), 2.18 (brd, J=33.3 Hz, 2H), 1.98 (brs, 2H)

Example 2.19: 1-(9H-carbazol-9-yl)-5-(pyrrolidin-1-yl)pentan-1-one hydrochloride 38.7 mg (0.11 mmol, 36% yield) of the title compound was prepared using the compound of Example 1.2 (100 mg, 0.30 mmol) and pyrrolidine (0.03 ml, 0.36 mmol) in accordance with the procedure of Example 2.1.

$^1$H NMR (400 MHz, CDCl$_3$) δ 11.66 (brs, 0.8H), 8.20 (d, J=8.3 Hz, 2H), 8.00 (d, J=7.2 Hz, 2H), 7.51-7.46 (m, 2H), 7.39 (t, J=7.3 Hz, 2H), 3.86-3.84 (m, 2H), 3.25 (t, J=6.7 Hz, 2H), 3.19-3.13 (m, 2H), 2.86-2.78 (m, 2H), 2.28-1.97 (m, 8H)

Example 2.20: 1-(9H-carbazol-9-yl)-5-(4-methylpiperidin-1-yl)pentan-1-one hydrochloride 44.2 mg (0.11 mmol, 38% yield) of the title compound was prepared using the compound of Example 1.2 (100 mg, 0.30 mmol) and 4-methylpiperidine (0.04 ml, 0.30 mmol) in accordance with the procedure of Example 2.1.

$^1$H NMR (400 MHz, CDCl$_3$) δ 11.89 (brs, 0.8H), 8.20 (d, J=8.4 Hz, 2H), 7.99 (dd, J=5.7 Hz, J=0.9 Hz, 2H), 7.48 (td, J=7.8 Hz, J=1.2 Hz, 2H), 7.41-7.37 (m, 2H), 3.59 (brd, J=11.4 Hz, 2H), 3.25 (t, J=6.7 Hz, 2H), 3.02 (quint, J=5.3 Hz, 2H), 2.63 (q, J=10.8 Hz, 2H), 2.18-2.13 (m, 2H), 2.09-1.94 (m, 5H), 1.81 (brd, J=14.0 Hz, 2H), 1.07-1.03 (m, 3H)

Example 2.21: 1-(9H-carbazol-9-yl)-5-(3-methylpiperidin-1-yl)pentan-1-one hydrochloride 59.5 mg (0.15 mmol, 51% yield) of the title compound was prepared using the compound of Example 1.2 (100 mg, 0.30 mmol) and 3-methylpiperidine (0.04 ml, 0.36 mmol) in accordance with the procedure of Example 2.1.

$^1$H NMR (400 MHz, CDCl$_3$) δ 11.26 (brs, 0.8H) 8.20 (d, J=8.4 Hz, 2H), 7.98 (d, J=7.1 Hz, 2H), 7.50-7.45 (m, 2H), 7.38 (t, J=7.3 Hz, 2H), 3.58 (brd, J=10.4 Hz, 1H), 3.48-3.44 (m, 1H), 3.24 (t, J=6.7 Hz, 2H), 3.05 (brt, J=7.6 Hz, 2H), 2.58-2.14 (m, 6H), 2.00-1.85 (m, 5H), 0.95 (m, J=6.2 Hz, 3H)

Example 2.22: 1-(9H-carbazol-9-yl)-5-(3,5-dimethylpiperidin-1-yl)pentan-1-one hydrochloride 60.6 mg (0.15 mmol, 50% yield) of the title compound was prepared using the compound of Example 1.2 (100 mg, 0.30 mmol) and 3,5-dimethylpiperidine (0.05 ml, 0.36 mmol) in accordance with the procedure of Example 2.1.

$^1$H NMR (400 MHz, CDCl$_3$) δ 12.16 (brs, 0.8H), 8.19 (d, J=8.3 Hz, 2H), 7.99 (d, J=7.3 Hz, 2H), 7.49-7.45 (m, 2H), 7.38 (t, J=7.3 Hz, 2H), 3.41 (brd, J=11.0 Hz, 2H), 3.24 (t, J=6.7 Hz, 2H), 3.01 (brt, J=7.9 Hz, 2H), 2.47 (brs, 2H), 2.16-2.09 (m, 4H), 1.97 (quint, J=7.2 Hz, 2H), 1.89 (brd, J=13.2 Hz, 2H), 0.94 (d, J=6.6 Hz, 6H)

Example 2.23: 5-(Azepan-1-yl)-1-(9H-carbazol-9-yl)pentan-1-one hydrochloride 37.0 mg (0.10 mmol, 32% yield) of the title compound was prepared using the compound of Example 1.2 (100 mg, 0.30 mmol) and hexamethyleneimine (0.04 ml, 0.36 mmol) in accordance with the procedure of Example 2.1.

$^1$H NMR (400 MHz, CDCl$_3$) δ 11.39 (brs, 0.8H), 8.19 (d, J=8.3 Hz, 2H), 7.98 (dd, J=5.7 Hz, J=0.9 Hz, 2H), 7.47 (t, J=7.3 Hz, 2H), 7.38 (t, J=7.4 Hz, 2H), 3.58 (brs, 2H), 3.24

(t, J=6.0 Hz, 2H), 3.09 (brs, 2H), 2.95 (brs, 2H), 2.18 (s, 4H), 1.98-1.97 (m, 2H), 1.86-1.83 (m, 4H), 1.63 (s, 2H)

Example 2.24: 1-(9H-carbazol-9-yl)-5-morpholinopentan-1-one hydrochloride 80.7 mg (0.22 mmol, 71% yield) of the title compound was prepared using the compound of Example 1.2 (100 mg, 0.30 mmol) and morpholine (0.03 ml, 0.36 mmol) in accordance with the procedure of Example 2.1.

$^1$H NMR (400 MHz, CDCl$_3$) δ 12.94 (brs, 0.8H), 8.18 (d, J=8.2 Hz, 2H), 7.98 (d, J=7.3 Hz, 2H), 7.47 (t, J=7.5 Hz, 2H), 7.38 (t, J=7.4 Hz, 2H), 4.32 (t, J=12.0 Hz, 2H). 3.97 (d, J=11.6 Hz, 2H), 3.48-3.43 (m, 2H), 3.25 (s, 2H), 3.07 (s, 2H), 2.88 (s, 2H), 2.17 (s, 2H), 2.00 (s, 2H)

Example 2.25: 1-(9H-carbazol-9-yl)-5-(4-phenylpiperidin-1-yl)pentan-1-one hydrochloride 109.2 mg (0.24 mmol, 81% yield) of the title compound was prepared using the compound of Example 1.2 (100 mg, 0.30 mmol) and 4-phenylpiperidine (73 mg, 0.45 mmol) in accordance with the procedure of Example 2.1.

$^1$H NMR (400 MHz, CDCl$_3$) δ 11.67 (brs, 0.8H), 8.21 (d, J=8.4 Hz, 2H), 7.99 (dd, J=5.8 Hz, J=0.8 Hz, 2H), 7.50-7.46 (m, 2H), 7.38 (td, J=7.5 Hz, J=0.7 Hz, 2H), 7.34-7.19 (m, 5H), 3.73 (brd, =10.4 Hz, 2H), 3.27 (t, J=6.7 Hz, 2H), 3.12-3.07 (m, 2H), 2.86-2.64 (m, 5H), 2.27-2.19 (m, 2H), 2.04-1.97 (m, 4H)

Example 2.26: 5-(4-Benzylpiperidin-1-yl)-1-(9H-carbazol-9-yl)pentan-1-one hydrochloride 113.5 mg (0.25 mmol, 81% yield) of the title compound was prepared using the compound of Example 1.2 (100 mg, 0.30 mmol) and 4-benzylpiperidine (0.06 ml, 0.36 mmol) in accordance with the procedure of Example 2.1.

$^1$H NMR (400 MHz, CDCl$_3$) δ 12.15 (brs, 0.8H), 8.18 (d, J=8.1 Hz, 2H), 7.98 (d, J=7.6 Hz, 2H), 7.46 (t, J=7.6 Hz, 2H), 7.37 (t, J=7.4 Hz, 2H), 7.29-7.17 (m, 3H), 7.11 (d, J=7.2 Hz, 2H), 3.57 (brd, J=9.8 Hz, 2H), 3.23 (s, 2H), 2.99 (s, 2H), 2.66-2.55 (m, 4H), 2.15-2.05 (m, 4H), 1.96 (s, 2H), 1.80 (d, J=13.5 Hz, 2H), 1.70 (brs, 1H)

Example 1.27: 5-(4-Acetylpiperazin-1-yl)-1-(9H-carbazol-9-yl)pentan-1-one hydrochloride 117.4 mg (0.28 mmol, 94% yield) of the title compound was prepared using the compound of Example 1.2 (100 mg, 0.30 mmol) and acetylpiperazine (47 mg, 0.36 mmol) in accordance with the procedure of Example 2.1.

$^1$H NMR (400 MHz, DMSO) δ 9.52 (brs, 0.8H), 8.29 (d, J=8.4 Hz, 2H), 8.21 (dd, J=5.8 Hz, J=0.8 Hz, 2H), 7.55-7.51 (m, 2H), 7.45-7.41 (m, 2H), 4.42 (brd, J=9.2 Hz, 1H), 4.01 (brd, J=14.4 Hz, 1H), 3.50 (brd, J=8.0 Hz, 2H), 3.41-3.32 (m, 2H), 3.20 (s, 2H), 3.04 (brd, J=10.0 Hz, 2H), 2.91 (brd, J=8.4 Hz, 2H), 2.03 (s, 3H), 1.83 (s, 4H)

Example 2.28: 1-(9H-carbazol-9-yl)-5-(4-methylpiperazin-1-yl)pentan-1-one hydrochloride 91.0 mg (0.24 mmol, 78% yield) of the title compound was prepared using the compound of Example 1.2 (100 mg, 0.30 mmol) and methylpiperazine (0.04 ml, 0.36 mmol) in accordance with the procedure of Example 2.1.

$^1$H NMR (400 MHz, DMSO) δ 11.61 (brs, 0.8H), 8.29 (d, J=8.4 Hz, 2H), 8.20 (dd, J=5.8 Hz, J=0.8 Hz, 2H), 7.55-7.50 (m, 2H), 7.44-7.40 (m, 2H), 3.32 (s, 9H), 3.16 (s, 3H), 2.72 (brs, 3H), 1.83 (s, 4H)

Example 2.29: 5-(4-Benzylpiperazinyl)-1-(9H-carbazol-9-yl)pentan-1-one hydrochloride 28.3 mg (0.06 mmol, 20% yield) of the title compound was prepared using the compound of Example 1.2 (100 mg, 0.30 mmol) and benzylpiperazine (0.06 ml, 0.36 mmol) in accordance with the procedure of Example 2.1.

$^1$H NMR (400 MHz, MeOD) δ 8.30 (d, J=8.4 Hz, 2H), 8.09 (d, J=7.6 Hz, 2H), 7.56 (brd, J=3.1 Hz, 2H), 7.52-7.48 (m, 5H), 7.43-7.39 (m, 2H), 4.34 (s, 2H), 3.82-3.21 (m, 12H), 2.00 (t, J=3.1 Hz, 4H)

Example 2.30: 1-(9H-carbazol-9-yl)-5-(4-(2-hydroxyphenyl)piperazin-1-yl)pentan-1-one hydrochloride 65.8 mg (0.14 mmol, 23% yield) of the title compound was prepared using the compound of Example 1.2 (100 mg, 0.30 mmol) and 1-(2-hydroxyphenyl)piperazine (162 mg, 0.91 mmol) in accordance with the procedure of Example 2.1.

$^1$H NMR (400 MHz, CDCl$_3$) δ 10.22 (brs, 0.8H), 8.31 (d, J=8.4 Hz, 2H), 8.20 (dd, J=5.7 Hz, J=0.8 Hz, 2H), 7.53 (td, J=7.8 Hz, J=1.2 Hz, 2H), 7.43 (t, J=7.2 Hz, 2H), 6.90-6.81 (m, 3H), 6.75 (td, J=7.4 Hz, J=1.6 Hz, 1H), 3.47 (brd, J=12.8 Hz, 3H), 3.39-3.33 (m, 4H), 3.22-3.15 (m, 4H), 3.00 (t, J=11.5 Hz, 2H), 1.89-1.85 (m, 4H)

Example 2.31: 1-(9H-carbazol-9-yl)-5-(4-(2-methoxyphenyl)piperazin-1-yl)pentan-1-one hydrochloride 43.1 mg (0.09 mmol, 30% yield) of the title compound was prepared using the compound of Example 1.2 (100 mg, 0.30 mmol) and 1-(2-methoxyphenyl)piperazine (0.06 ml, 0.36 mmol) in accordance with the procedure of Example 2.1.

$^1$H NMR (300 MHz, DMSO) δ 10.62 (brs, 0.8H), 8.32 (d, J=8.3 Hz, 2H), 8.22 (d, J=7.5 Hz, 2H), 7.56-7.51 (m, 2H), 7.43 (t, J=7.4 Hz, 2H), 7.05-6.87 (m, 4H), 3.79 (s, 3H), 3.53 (q, J=10.4 Hz, 4H), 3.35 (t, J=6.3 Hz, 2H), 3.23-3.02 (m, 6H), 1.91-1.85 (m, 4H)

Example 2.32: 4-(4-Benzylpiperazin-1-yl)-1-(9H-carbazol-9-yl)butan-1-one hydrochloride 27.7 mg (0.06 mmol, 17% yield) of the title compound was prepared using the compound of Example 1.3 (100 mg, 0.37 mmol) and benzylpiperazine (0.08 ml, 0.44 mmol) in accordance with the procedure of Example 2.1.

$^1$H NMR (400 MHz, CDCl$_3$) δ 11.47 (brs, 0.8H), 8.33 (d, J=8.4 Hz, 2H), 8.20 (d, J=7.0 Hz, 2H), 7.59 (s, 3H), 7.54-7.49 (m, 2H), 7.44-7.41 (m, 4H), 4.30 (brs, 4H), 3.73-3.08 (m, 6H), 2.42 (t, J=7.3 Hz, 2H), 2.21-2.20 (m, 2H), 1.95-1.89 (m, 2H)

Example 2.33: 1-(9H-carbazol-9-yl)-4-(4-(2-hydroxyphenyl)piperazin-1-yl)butan-1-one 148.1 mg (0.36 mmol, 49% yield) of the title compound was prepared using the compound of Example 1.3 (200 mg, 0.74 mmol) and 1-(2-hydroxyphenyl)piperazine (197 mg, 1.10 mmol) in accordance with the procedure of Example 2.1.

$^1$H NMR (400 MHz, CDCl$_3$) δ 8.27 (d, J=8.4 Hz, 2H), 8.03-8.01 (m, 2H), 7.52-7.47 (m, 2H), 7.40 (td, J=7.5 Hz, J=0.8 Hz, 2H), 7.08-7.03 (m, 2H), 6.93 (dd, J=6.0 Hz, J=1.2 Hz, 1H), 6.85-6.81 (m, 1H), 3.25 (t, J=7.0 Hz, 2H), 2.81 (t, J=4.7 Hz, 4H), 2.61 (t, J=7.0 Hz, 6H), 2.17 (quint, J=7.0 Hz, 2H)

Example 2.34: 1-(9H-carbazol-9-yl)-4-(4-(2-methoxyphenyl)piperazin-1-yl)butan-1-one 78 mg (0.18 mmol, 50% yield) of the title compound was prepared using the compound of Example 1.3 (100 mg, 0.37 mmol) and 1-(2-hydroxyphenyl)piperazine (197 mg, 1.10 mmol) in accordance with the procedure of Example 2.1.

$^1$H NMR (400 MHz, CDCl$_3$) δ 8.25 (d, J=8.4 Hz, 2H), 7.98 (d, J=7.6 Hz, 2H), 7.48-7.44 (m, 2H), 7.36 (t, J=7.4 Hz, 2H), 7.00-6.94 (m, 1H), 6.92-6.87 (m, 2H), 6.84 (d, J=7.9 Hz, 1H), 3.21 (t, J=7.1 Hz, 2H), 3.06 (s, 4H), 2.69 (s, 4H), 2.60 (t, J=7.0 Hz, 2H), 2.16 (quint, J=7.1 Hz, 2H)

Example 2.35: N-Butyl-6-(9H-carbazol-9-yl)-N-methylhexane-1-amine

The compound of Example 1.4 (100 mg, 0.30 mmol) and N-methylbutylamine (0.04 ml, 0.36 mmol) were dissolved in acetonitrile (10 ml) in a reactor. The solution was heated to reflux at 40° C. until the next day. After completion of the reaction, the reaction mixture was diluted with CH$_2$C$_{12}$, and H$_2$O were then added thereto. The aqueous layer was extracted with CH$_2$C$_{12}$. The obtained organic layer was dried over anhydrous Na$_2$SO$_4$ and filtered. The filtrate was concentrated under reduced pressure. The concentrate was purified by silica gel column chromatography (MC:MeOH=20:1), giving 68 mg (0.20 mmol, 67% yield) of the final title compound.

$^1$H NMR (400 MHz, CDCl$_3$) δ 8.06 (d, J=7.7 Hz, 2H), 7.45-7.40 (m, 2H), 7.36 (d, J=8.2 Hz, 2H), 7.22-7.18 (m, 2H), 4.25 (t, J=6.9 Hz, 2H), 2.82-2.71 (m, 4H), 2.54 (s, 3H), 1.83 (quint, J=7.2 Hz, 2H), 1.71-1.61 (m, 4H), 1.35-1.20 (m, 6H), 0.90 (t, J=7.4 Hz, 3H)

Example 2.36: N-Benzyl-6-(9H-carbazol-9-yl)-N-methylhexane-1-amine 111.0 mg (0.30 mmol, 99% yield) of the title compound was prepared using the compound of Example 1.4 (100 mg, 0.30 mmol) and N-benzylmethylamine (0.05 ml, 0.36 mmol) in accordance with the procedure of Example 2.35.

$^1$H NMR (400 MHz, CDCl$_3$) δ 8.06 (d, J=7.6 Hz, 2H), 7.44-7.39 (m, 2H), 7.34 (d, J=8.2 Hz, 2H), 7.29-7.24 (m, 4H), 7.23-7.17 (m, 3H), 4.21 (t, J=7.2 Hz, 2H), 3.40 (s, 2H), 2.26 (t, J=7.3 Hz, 2H), 2.11 (s, 3H), 1.80 (quint, J=7.2 Hz, 2H), 1.42 (quint, J=7.1 Hz, 2H), 1.36-1.24 (m, 4H)

Example 2.37: 9-(6-(Pyrrolidin-1-yl)hexyl)-9H-carbazole 61.4 mg (0.19 mmol, 63% yield) of the title compound was prepared using the compound of Example 1.4 (100 mg, 0.30 mmol) and pyrrolidine (0.03 ml, 0.36 mmol) in accordance with the procedure of Example 2.35.

$^1$H NMR (400 MHz, CDCl$_3$) δ 8.08 (d, J=7.7 Hz, 2H), 7.47-7.43 (m, 2H), 7.38 (d, J=8.2 Hz, 2H), 7.23-7.19 (m, 2H), 4.28 (t, J=6.8 Hz, 2H), 3.07 (brs, 3H), 2.78-2.74 (m, 2H), 2.04-2.02 (m, 4H), 1.84 (quint, J=7.2 Hz, 2H), 1.75-1.67 (m, 2H), 1.36-1.22 (m, 5H)

Example 2.38: 9-(6-(4-Methylpiperidin-1-yl)hexyl)-9H-carbazole 103 mg (0.30 mmol, 98% yield) of the title compound was prepared using the compound of Example 1.4 (100 mg, 0.30 mmol) and 4-methylpiperidine (0.04 ml, 0.36 mmol) in accordance with the procedure of Example 2.35.

$^1$H NMR (400 MHz, CDCl$_3$) δ 8.08 (d, J=7.7 Hz, 2H), 7.45-7.41 (m, 2H), 7.37 (d, J=8.1 Hz, 2H), 7.22-7.18 (m, 2H), 4.26 (t, J=7.2 Hz, 2H), 2.83 (brd, J=11.6 Hz, 2H), 2.22 (t, J=7.7 Hz, 2H), 1.88-1.80 (m, 4H), 1.58 (brd, J=12.6 Hz, 2H), 1.48-1.17 (m, 9H), 0.89 (d, J=6.1 Hz, 3H)

Example 2.39: 9-(6-(3-Methylpiperidin-1-yl)hexyl)-9H-carbazole 98.0 mg (0.28 mmol, 93% yield) of the title compound was prepared using the compound of Example 1.4 (100 mg, 0.30 mmol) and 3-methylpiperidine (0.04 ml, 0.36 mmol) in accordance with the procedure of Example 2.35.

$^1$H NMR (400 MHz, CDCl$_3$) δ 8.08 (d, J=7.7 Hz, 2H), 7.46-7.42 (m, 2H), 7.37 (d, J=8.2 Hz, 2H), 7.23-7.18 (m, 2H), 4.25 (t, J=7.1 Hz, 2H), 2.89-2.82 (m, 2H), 2.28 (t, J=7.9 Hz, 2H), 1.86-1.58 (m, 8H), 1.55-1.45 (m, 2H), 1.40-1.24 (m, 5H), 0.83 (d, J=6.5 Hz, 3H)

Example 2.40: 9-(6-(3,5-Dimethylpiperidin-1-yl)hexyl)-9H-carbazole 91.3 mg (0.25 mmol, 83% yield) of the title compound was prepared using the compound of Example 1.4 (100 mg, 0.30 mmol) and 3,5-dimethylpiperidine (0.05 ml, 0.36 mmol) in accordance with the procedure of Example 2.35.

$^1$H NMR (400 MHz, CDCl$_3$) δ 8.07 (d, J=7.7 Hz, 2H), 7.45-7.41 (m, 2H), 7.35 (d, J=8.2 Hz, 2H), 7.20 (td, J=7.4 Hz, J=0.9 Hz, 2H), 4.23 (t, J=7.1 Hz, 2H), 2.80 (brdt, J=10.5 Hz, J=1.7 Hz, 2H), 2.25-2.21 (m, 2H), 1.88-1.65 (m, 5H), 1.50-1.22 (m, 9H), 0.92 (d, J=6.8 Hz, 1H), 0.81 (d, J=6.5 Hz, 5H)

Example 2.41: 9-(6-(Azepan-1-yl)hexyl)-9H-carbazole 57.5 mg (0.16 mmol, 54% yield) of the title compound was prepared using the compound of Example 1.4 (100 mg, 0.30 mmol) and hexamethyleneimine (0.04 ml, 0.36 mmol) in accordance with the procedure of Example 2.35.

$^1$H NMR (400 MHz, CDCl$_3$) δ 8.06 (d, J=7.7 Hz, 2H), 7.45-7.41 (m, 2H), 7.36 (d, J=8.2 Hz, 2H), 7.22-7.18 (m, 2H), 4.25 (t, J=6.9 Hz, 2H), 3.03 (brs, 3H), 2.75-2.71 (m, 2H), 1.86-1.63 (m, 12H), 1.35-1.18 (m, 5H)

Example 2.42: 4-(6-(9H-carbazol-9-yl)hexyl)morpholine 97.0 mg (0.29 mmol, 95% yield) of the title compound was prepared using the compound of Example 1.4 (100 mg, 0.30 mmol) and morpholine (0.03 ml, 0.36 mmol) in accordance with the procedure of Example 2.35.

$^1$H NMR (400 MHz, CDCl$_3$) δ 8.06 (d, J=7.8 Hz, 2H), 7.42 (t, J=7.6 Hz, 2H), 7.35 (d, J=8.1 Hz, 2H), 7.19 (t, J=7.4 Hz, 2H), 4.23 (t, J=7.1 Hz, 2H), 3.66 (t, J=4.5 Hz, 4H), 2.33 (s, 4H), 2.21 (t, J=7.5 Hz, 2H), 1.82 (quint, J=7.2 Hz, 2H), 1.43-1.27 (m, 6H)

Example 2.43: 9-(6-(4-Phenylpiperidin-1-yl)hexyl)-9H-carbazole 92.9 mg (0.21 mmol, 69% yield) of the title compound was prepared using the compound of Example 1.4 (100 mg, 0.30 mmol) and 4-phenylpiperidine (59 mg, 0.36 mmol) in accordance with the procedure of Example 2.35.
$^1$H NMR (400 MHz, CDCl$_3$) δ 8.06-8.04 (m, 2H), 7.44-7.39 (m, 2H), 7.34 (d, J=8.2 Hz, 2H), 7.27-7.16 (m, 7H), 4.22 (t, J=7.0 Hz, 2H), 3.15 (brd, J=11.6 Hz, 2H), 2.54-2.44 (m, 3H), 2.25 (brt, J=11.3 Hz, 2H), 2.16-2.05 (m, 2H), 1.84-1.79 (m, 4H), 1.61-1.53 (m, 2H), 1.35-1.18 (m, 4H)

Example 2.44: 9-(6-(4-Benzylpiperidin-1-yl)hexyl)-9H-carbazole 83.0 mg (0.18 mmol, 59% yield) of the title compound was prepared using the compound of Example 1.4 (100 mg, 0.30 mmol) and 4-benzylpiperidine (0.06 mg, 0.36 mmol) in accordance with the procedure of Example 2.35.
$^1$H NMR (400 MHz, CDCl$_3$) δ 8.05 (d, J=7.7 Hz, 2H), 7.41 (td, J=7.6 Hz, J=1.1 Hz, 2H), 7.33 (d, J=8.2 Hz, 2H), 7.25-7.13 (m, 5H), 7.10-7.08 (m, 2H), 4.20 (t, J=7.1 Hz, 2H), 2.84 (brd, J=11.7 Hz, 2H), 2.48 (d, J=7.0 Hz, 2H), 2.20 (t, J=7.9 Hz, 2H), 1.83-1.76 (m, 4H), 1.57 (brd, J=12.8 Hz, 2H), 1.50-1.19 (m, 9H)

Example 2.45: 1-(4-(6-(9H-carbazol-9-yl)hexyl)piperazin-1-yl)ethanone 103.6 mg (0.27 mmol, 91% yield) of the title compound was prepared using the compound of Example 1.4 (100 mg, 0.30 mmol) and acetylpiperazine (47 mg, 0.36 mmol) in accordance with the procedure of Example 2.35.
$^1$H NMR (400 MHz, CDCl$_3$) δ 8.07 (d, J=7.6 Hz, 2H), 7.44-7.40 (m, 2H), 7.35 (d, J=8.2 Hz, 2H), 7.22-7.18 (m, 2H), 4.24 (t, J=7.1 Hz, 2H), 3.55 (t, J=5.1 Hz, 2H), 3.34 (t, J=5.1 Hz, 2H), 2.27 (t, J=4.6 Hz, 4H), 2.20 (t, J=7.4 Hz, 2H), 2.02 (s, 3H), 1.83 (quint, J=7.3 Hz, 2H), 1.41-1.21 (m, 6H)

Example 2.46: 9-(6-(4-Methylpiperazin-1-yl)hexyl)-9H-carbazole 62.0 mg (0.18 mmol, 59% yield) of the title compound was prepared using the compound of Example 1.4 (100 mg, 0.30 mmol) and methylpiperazine (0.04 ml, 0.36 mmol) in accordance with the procedure of Example 2.35.
$^1$H NMR (400 MHz, CDCl$_3$) δ 8.08 (d, J=7.7 Hz, 2H), 7.44 (t, J=7.6 Hz, 2H), 7.37 (d, J=8.1 Hz, 2H), 7.23-7.19 (m, 2H), 4.26 (t, J=7.1 Hz, 2H), 2.43 (brs, 10H), 2.28-2.24 (m, 3H), 1.85 (quint, J=7.3 Hz, 2H), 1.47-1.25 (m, 6H)

Example 2.47: 9-(6-(4-Benzylpiperazin-1-yl)hexyl)-9H-carbazole 111.2 mg (0.24 mmol, 79% yield) of the title compound was prepared using the compound of Example 1.4 (100 mg, 0.30 mmol) and benzylpiperazine (0.06 ml, 0.36 mmol) in accordance with the procedure of Example 2.35.
$^1$H NMR (400 MHz, CDCl$_3$) δ 8.07-8.05 (m, 2H), 7.44-7.40 (m, 2H), 7.34 (d, J=8.2 Hz, 2H), 7.30-7.19 (m, 7H), 4.23 (t, J=7.2 Hz, 2H), 3.47 (s, 2H), 2.42 (brs, 8H), 2.23 (t, J=7.6 Hz, 2H), 1.82 (quint, J=7.3 Hz, 2H), 1.44-1.23 (m, 6H)

Example 2.48: 2-(4-(6-(9H-carbazol-9-yl)hexyl)piperazin-1-yl)phenol 111.2 mg (0.26 mmol, 86% yield) of the title compound was prepared using the compound of Example 1.4 (100 mg, 0.30 mmol) and 1-(2-hydroxyphenyl)piperazine (81 mg, 0.45 mmol) in accordance with the procedure of Example 2.35.
$^1$H NMR (400 MHz, CDCl$_3$) δ 8.06 (d, J=7.7 Hz, 2H), 7.43-7.39 (m, 2H), 7.34 (d, J=8.2 Hz, 2H), 7.20-7.16 (m, 2H), 7.10 (dd, J=5.9 Hz, J=1.5 Hz, 1H), 7.02 (td, J=7.7 Hz, J=1.3 Hz, 1H), 6.92 (dd, J=6.0 Hz, J=1.4 Hz, 1H), 6.81 (td, J=7.6 Hz, J=1.5 Hz, 1H), 4.21 (t, J=7.1 Hz, 2H), 2.83 (t, J=4.7 Hz, 4H), 2.48 (brs, 3H), 2.26 (t, J=7.6 Hz, 2H), 1.82 (quint, J=7.3 Hz, 2H), 1.44-1.25 (m, 7H)

Example 2.49: 9-(6-(4-(2-Methoxyphenyl)piperazin-1-yl)hexyl)-9H-carbazole 650 mg (1.47 mmol, 49% yield) of the title compound was prepared using 1-(2-methoxyphenyl)piperazine (699 mg, 3.64 mmol), the compound of Example 1.4 (1 g, 3.03 mmol), and K$_2$CO$_3$ (418 mg, 3.03 mmol) in accordance with the procedure of Example 235
$^1$H NMR (400 MHz, CDCl$_3$) δ 8.23 (d, J=7.2 Hz, 2H), 7.58 (t, J=7.6 Hz, 2H), 7.50 (d, J=8.1 Hz, 2H), 7.36 (t, J=7.4 Hz, 2H), 7.13-7.04 (m, 3H), 6.95 (d, J=7.7 Hz, 1H), 4.35 (t, J=7.0 Hz, 2H), 3.94 (s, 3H), 3.21 (brs, 4H), 2.73 (brs, 4H), 2.46 (t, J=7.5 Hz, 2H), 1.99-1.94 (m, 2H), 1.60-1.47 (m, 4H)

Example 2.50: 9-(5-(4-Phenylpiperidin-1-yl)pentyl)-9H-carbazole 226.4 mg (0.52 mmol, 83% yield) of the title compound was prepared using the compound of Example 1.5 (200 mg, 0.63 mmol) and 4-phenylpiperidine (153 mg, 0.95 mmol) in accordance with the procedure of Example 2.35.
$^1$H NMR (400 MHz, CDCl$_3$) δ 8.04 (d, J=7.7 Hz, 2H), 7.42-7.38 (m, 2H), 7.32 (d, J=8.2 Hz, 2H), 7.24-7.12 (m, 7H), 4.18 (t, J=6.8 Hz, 2H), 3.10 (brd, J=11.7 Hz, 2H), 2.52-2.41 (m, 3H), 2.29 (t, J=11.4 Hz, 2H), 2.16-2.05 (m, 2H), 1.82-1.73 (m, 4H), 1.63-1.55 (m, 2H), 1.22 (quint, J=7.7 Hz, 2H)

Example 2.51: 9-(5-(4-Benzylpiperazin-1-yl)pentyl)-9H-carbazole 248.0 mg (0.60 mmol, 95% yield) of the title compound was prepared using the compound of Example 1.5 (200 mg, 0.63 mmol) and benzylpiperazine (0.13 ml, 0.76 mmol) in accordance with the procedure of Example 2.35.
$^1$H NMR (400 MHz, CDCl$_3$) δ 8.04 (d, J=7.7 Hz, 2H), 7.41-7.37 (m, 2H), 7.30 (d, J=8.2 Hz, 2H), 7.26-7.15 (m, 7H), 4.17 (t, J=7.1 Hz, 2H), 3.44 (s, 2H), 2.39 (brs, 8H), 2.19 (t, J=7.7 Hz, 2H), 1.79 (quint, J=7.4 Hz, 2H), 1.43 (quint, J=7.6 Hz, 2H), 1.28 (quint, J=7.6 Hz, 2H)

Example 2.52: 2-(4-(5-(9H-carbazol-9-yl)pentyl)piperazin-1-yl)phenol 172.3 mg (0.42 mmol, 66% yield) of the title compound was prepared using the compound of Example 1.5 (200 mg, 0.63 mmol) and 1-(2-hydroxyphenyl)piperazine (169 mg, 0.95 mmol) in accordance with the procedure of Example 2.35.
$^1$H NMR (400 MHz, CDCl$_3$) δ 8.04 (d, J=7.7 Hz, 2H), 7.42-7.38 (m, 2H), 7.31 (d, J=8.2 Hz, 2H), 7.19-7.15 (m, 2H), 7.09-7.06 (m, 1H), 7.03-6.99 (m, 1H), 6.92 (dd, J=6.0 Hz, J=1.5 Hz, 1H), 6.80 (td, J=7.6 Hz, J=1.5 Hz, 1H), 4.16 (t, J=7.1 Hz, 2H), 2.79 (t, J=4.7 Hz, 4H), 2.41 (brs, 4H), 2.20

(t, J=7.6 Hz, 2H), 1.79 (quint, J=7.4 Hz, 2H), 1.41 (quint, J=7.5 Hz, 2H), 1.32-1.24 (m, 2H)

Example 2.53: 9-(5-(4-(2-Methoxyphenyl)piperazin-1-yl)pentyl)-9H-carbazole 247.7 mg (0.58 mmol, 92% yield) of the title compound was prepared using the compound of Example 1.5 (200 mg, 0.63 mmol) and 1-(2-methoxyphenyl)piperazine (0.13 ml, 0.76 mmol) in accordance with the procedure of Example 2.35.

$^1$H NMR (400 MHz, CDCl$_3$) δ 8.05 (d, J=7.7 Hz, 2H), 7.43-7.39 (m, 2H), 7.32 (d, J=8.2 Hz, 2H), 7.20-7.16 (m, 2H), 6.95-6.84 (m, 3H), 6.77 (d, J=7.6 Hz, 1H), 4.18 (t, J=7.1 Hz, 2H), 3.76 (s, 3H), 3.04 (brs, 4H), 2.55 (brs, 4H), 2.27 (t, J=7.7 Hz, 2H), 1.81 (quint, J=7.4 Hz, 2H), 1.48 (quint, J=7.6 Hz, 2H), 1.31 (quint, J=7.6 Hz, 2H)

Example 2.54: 9-(4-(4-Phenylpiperidin-1-yl)butyl)-9H-carbazole 213.5 mg (0.56 mmol, 84% yield) of the title compound was prepared using the compound of Example 1.6 (200 mg, 0.66 mmol) and 4-phenylpiperidine (160 mg, 0.99 mmol) in accordance with the procedure of Example 2.35.

$^1$H NMR (400 MHz, CDCl$_3$) δ 8.02 (d, J=7.7 Hz, 2H), 7.40-7.36 (m, 2H), 7.30 (d, J=8.2 Hz, 2H), 7.23-7.09 (m, 7H), 4.14 (t, J=7.2 Hz, 2H), 2.85 (brd, J=11.2 Hz, 2H), 2.36-2.29 (m, 1H), 2.21 (t, J=7.5 Hz, 2H), 1.87-1.67 (m, 8H), 1.49 (quint, J=7.6 Hz, 2H)

Example 2.55: 2-(4-(4-(9H-carbazol-9-yl)butyl)piperazin-1-yl)phenol 104.5 mg (0.26 mmol, 40% yield) of the title compound was prepared using the compound of Example 1.6 (200 mg, 0.66 mmol) and 1-(2-hydroxyphenyl)piperazine (177 mg, 0.99 mmol) in accordance with the procedure of Example 2.35.

$^1$H NMR (400 MHz, CDCl$_3$) δ 8.06 (d, J=7.7 Hz, 2H), 7.45-7.41 (m, 2H), 7.37 (d, J=8.1 Hz, 2H), 7.22-7.18 (m, 2H), 7.09 (dd, J=5.9 Hz, J=1.5 Hz, 1H), 7.05-7.01 (m, 1H), 6.92 (dd, J=6.0 Hz, J=1.4 Hz, 1H), 6.81 (td, J=7.6 Hz, J=1.5 Hz, 1H) 4.25 (t, J=7.1 Hz, 2H), 2.80 (t, J=4.7 Hz, 4H), 2.45 (brs, 4H), 2.31 (t, J=7.4 Hz, 2H), 1.86 (quint, J=7.4 Hz, 2H), 1.52 (quint, J=7.5 Hz, 2H)

Example 2.56: 9-(4-(4-(2-Methoxyphenyl)piperazin-1-yl)butyl)-9H-carbazole 256.4 mg (0.62 mmol, 94% yield) of the title compound was prepared using the compound of Example 1.6 (200 mg, 0.66 mmol) and 1-(2-methoxyphenyl)piperazine (0.14 ml, 0.79 mmol) in accordance with the procedure of Example 2.35.

$^1$H NMR (400 MHz, CDCl$_3$) δ 8.04 (d, J=7.7 Hz, 2H), 7.42-7.38 (m, 2H), 7.33 (d, J=8.1 Hz, 2H), 7.19-7.15 (m, 2H), 6.95-6.88 (m, 1H), 6.85 (d, J=4.0 Hz, 2H), 6.75 (d, J=7.8 Hz, 1H), 4.18 (t, J=7.2 Hz, 2H), 3.74 (s, 3H), 3.00 (brs, 4H), 2.50 (brs, 4H), 2.31 (t, J=7.4 Hz, 2H), 1.81 (quint, J=7.4 Hz, 2H), 1.50 (quint, J=7.5 Hz, 2H)

Example 2.57: 9-(3-(4-Phenylpiperidin-1-yl)propyl)-9H-carbazole 132.9 mg (0.36 mmol, 52% yield) of the title compound was prepared using the compound of Example 1.7 (200 mg, 0.69 mmol) and 4-benzylpiperidine (168 mg, 1.04 mmol) in accordance with the procedure of Example 2.35.

$^1$H NMR (400 MHz, CDCl$_3$) δ 8.06 (dt, J=7.7 Hz, J=0.8 Hz, 2H), 7.46-7.40 (m, 4H), 7.29-7.26 (m, 2H), 7.23-7.15 (m, 5H), 4.32 (t, J=6.7 Hz, 2H), 2.90 (brd, J=11.5 Hz, 2H), 2.46-2.38 (m, 1H), 2.27 (t, J=6.8 Hz, 2H), 1.99 (quint, J=6.8 Hz, 2H), 1.93-1.85 (m, 2H), 1.83-1.71 (m, 4H)

Example 2.58: 9-(3-(4-Benzylpiperazin-1-yl)propyl)-9H-carbazole 204.6 mg (0.53 mmol, 77% yield) of the title compound was prepared using the compound of Example 1.7 (200 mg, 0.69 mmol) and benzylpiperazine (0.14 ml, 0.83 mmol) in accordance with the procedure of Example 2.35.

$^1$H NMR (400 MHz, CDCl$_3$) δ 8.04-8.02 (m, 2H), 7.41-7.36 (m, 4H), 7.30-7.24 (m, 4H), 7.23-7.14 (m, 3H), 4.26 (t, J=6.7 Hz, 2H), 3.46 (s, 2H), 2.39 (brd, J=41.2 Hz, 8H), 2.21 (t, J=6.8 Hz, 2H), 1.92 (quint, J=6.7 Hz, 2H)

Example 2.59: 2-(4-(3-(9H-carbazol-9-yl)propyl)piperazin-1-yl)phenol 131.6 mg (0.34 mmol, 60% yield) of the title compound was prepared using the compound of Example 1.7 (176 mg, 0.61 mmol) and 1-(2-hydroxyphenyl)piperazine (153 mg, 0.86 mmol) in accordance with the procedure of Example 2.35.

$^1$H NMR (400 MHz, CDCl$_3$) δ 8.07 (d, J=7.7 Hz, 2H), 7.46-7.41 (m, 4H), 7.24-7.15 (m, 3H), 7.08-7.03 (m, 1H), 6.94 (dd, J=6.0 Hz, J=1.4 Hz, 1H), 6.85 (td, J=7.6 Hz, J=1.5 Hz, 1H), 4.36 (t, J=6.6 Hz, 2H), 2.85 (t, J=4.7 Hz, 4H), 2.47 (brs, 4H), 2.30 (t, J=6.7 Hz, 2H), 2.01 (quint, J=6.6 Hz, 2H)

Example 2.60: 9-(3-(4-(2-Methoxyphenyl)piperazin-1-yl)propyl)-9H-carbazole 145.8 mg (0.36 mmol, 60% yield) of the title compound was prepared using the compound of Example 1.7 (176 mg, 0.61 mmol) and 1-(2-methoxyphenyl)piperazine (0.13 ml, 0.73 mmol) in accordance with the procedure of Example 2.35.

$^1$H NMR (400 MHz, CDCl$_3$) δ 8.04 (d, J=7.8 Hz, 2H), 7.43-7.37 (m, 4H), 7.19-7.15 (m, 2H), 6.96-6.86 (m, 3H), 6.78-6.76 (m, 1H), 4.29 (t, J=6.6 Hz, 2H), 3.75 (s, 3H), 3.06 (brs, 4H), 2.50 (brs, 4H), 2.26 (t, J=6.7 Hz, 2H), 1.94 (quint, J=6.6 Hz, 2H)

Formulation Examples

The inventive carbazole derivatives can be formulated into various dosage forms according to the intended purpose. Exemplary formulations containing the carbazole derivatives or pharmaceutically acceptable salts thereof as an active ingredient are provided hereinbelow. However, these formulation examples are merely illustrative and the scope of the present invention is not limited thereto.

Formulation Example 1: Tablets (Direct Compression)

5.0 mg of the compound prepared in Example 2.15 was sieved and mixed with 14.1 mg of lactose, 0.8 mg of crospovidone USNF, and 0.1 mg of magnesium stearate. The mixture was compressed into tablets.

Formulation Example 2: Tablets (Wet Granulation)

5.0 mg of the compound prepared in Example 2.15 was sieved and mixed with 16.0 mg of lactose and 4.0 mg of starch. To the mixture was added an appropriate amount of a solution of 0.3 mg of polysorbate 80 in pure water. The resulting mixture was granulated. After drying, the granules were sieved and mixed with 2.7 mg of colloidal silicon dioxide and 2.0 mg of magnesium stearate. The mixture was compressed into tablets.

Formulation Example 3: Powders and Capsules 5.0 mg of the compound prepared in Example 2.15 was sieved and mixed with 14.8 mg of lactose, 10.0 mg of polyvinylpyrrolidone, and 0.2 mg of magnesium stearate. The mixture was filled in hard No. 5 gelatin capsules using a proper device.

Formulation Example 4: Injectable Preparations 100 mg of the compound prepared in Example 2.15, 180 mg of mannitol, 26 mg of $Na_2HPO_4 \cdot 12H_2O$, and 2,974 mg of distilled water were mixed to produce injectable preparations.

Experimental Example 1: Measurement of Binding Affinity for the 5-$HT_7$ Serotonin Receptor In this example, the human gene recombinant 5-$HT_7$ receptor expressed in CHO cells was used. 1 nM [$^3$H]LSD, 5-$HT_7$ receptor membrane (15 μg/well), a test drug, 10 mM $MgCl_2$, 50 mM Tris-HCl buffer (pH 7.4) containing 0.1 mM EDTA, etc. were added to a vessel until the final volume reached 0.25 ml. The test drug was used at various concentrations. The mixture was cultured at 25° C. for 90 min. The culture was rapidly filtered through a Whatman GF/C glass fiber filter, which had been previously wetted with 0.3% polyethyleneimine using a Brandel harvester, to quench the reaction. The reaction mixture was washed with cold 50 mM Tris-HCl buffer. The filter was covered with MeltiLex, sealed in a sample bag, and dried in an oven. Counting was performed using MicroBeta (Wallac) and nonspecific binding was measured in the presence of 0.5 mianserin. The K value of the test drug was obtained from nonlinear regression analysis (GraphPad Prism Program, San Diego, USA) of isotherms obtained by repeatedly performing the experiment on the drug at 10-11 stage concentrations in two test tubes (each twice).

The % inhibition values of the inventive compounds having different Y structures at a concentration of 10 μM against the 5-$HT_7$ serotonin receptor were measured. Further, the binding affinity ($K_i$) values of the inventive compounds having different Y structures at a concentration of 10 μM for the 5-$HT_7$ serotonin receptor were measured. The results are shown in Tables 1 to 3.

TABLE 1

| Example No. | Y (structure) | 5-$HT_7$ % inhibition | 5-$HT_7$ Ki (nM) | 5-$HT_{1E}$ % inhibition | 5-$HT_{1E}$ Ki (nM) | 5-$HT_{2C}$ % inhibition | 5-$HT_{2C}$ Ki (nM) |
|---|---|---|---|---|---|---|---|
| Example 2.1 | | 82.8 | 680 | 51.3 | — | 87.4 | 207 |
| Example 2.17 | | 50.0 | 1281 | 73.9 | — | — | — |
| Example 2.35 | | 70.7 | 511 | 55.7 | — | 59.4 | — |
| Example 2.2 | | 92.0 | 604 | 10.2 | — | 54.6 | 1315 |
| Example 2.18 | | 83.1 | 513 | −22.5 | — | 32.6 | — |
| Example 2.36 | | 64.0 | 1980 | −13.2 | — | — | — |
| Example 2.3 | | 74.0 | 1051 | 13.9 | — | 76.7 | 764 |
| Example 2.19 | | 57.4 | 2157 | 16.3 | — | 45.0 | — |
| Example 2.37 | | 66.9 | 1546 | 21.1 | — | — | — |
| Example 2.7 | | 86.0 | 616 | 1.8 | — | 77.2 | 411 |
| Example 2.23 | | 77.0 | 949 | −11.7 | — | 55.0 | 1088 |
| Example 2.41 | | 71.3 | 952 | 2.7 | — | — | — |
| Example 2.4 | | 94.2 | 364 | −11.6 | — | 78.5 | 878 |
| Example 2.20 | | 80.2 | 592 | −19.3 | — | 44.4 | — |
| Example 2.38 | | 82.9 | 597 | −9.4 | — | — | — |
| Example 2.5 | | 84.6 | 550 | −15.3 | — | 86.6 | 486 |
| Example 2.21 | | 69.4 | 883 | −6.0 | — | 50.0 | — |
| Example 2.39 | | 75.6 | 909 | 1.5 | — | — | — |

TABLE 1-continued

| Example No. | Y (structure) | 5-HT$_7$ % inhibition | 5-HT$_7$ Ki (nM) | 5-HT$_{1E}$ % inhibition | 5-HT$_{1E}$ Ki (nM) | 5-HT$_{2C}$ % inhibition | 5-HT$_{2C}$ Ki (nM) |
|---|---|---|---|---|---|---|---|
| Example 2.6 | 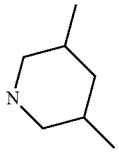 | 77.2 | 833 | −21.9 | — | 80.6 | 454 |
| Example 2.22 | | 67.6 | 1398 | −10.5 | — | 52.1 | 852 |
| Example 2.40 | | 57.7 | 1598 | −7.3 | — | — | — |

Referring to the results in Table 1, the compounds wherein Y is NR$_1$R$_2$ (R$_1$ and R$_2$ are alkyl groups that are not bonded to each other and cannot form a ring) showed good inhibitory effects on both 5-HT$_7$ and 5-HT$_{2C}$, and particularly, they showed very good inhibitory effects on 5-HT$_{1E}$ compared to the other carbazole compounds.

Meanwhile, the compounds wherein Y is NR$_1$R$_2$ and (R$_1$ and R$_2$ are not bonded to each other and cannot form a ring and either R$_1$ or R$_2$ is a benzyl group) and the compounds wherein Y is NR$_1$R$_2$ (R$_1$ and R$_2$ are bonded to each other to form a ring) showed no inhibitory effects on 5-HT$_{1E}$ but showed good inhibitory effects on 5-HT$_7$ and 5-HT$_{2C}$. Particularly, the compounds in which the alkyl chain between X and Y consists of 5 carbon atoms had significantly high % inhibition values against 5-HT$_{2C}$.

Referring to the results in Table 2, the compounds wherein Y is a substituted piperidinyl group were found to have very high % inhibition values of 89.9 to 103.0 against 5-HT$_7$, together with good inhibitory effects on 5-HT$_{2C}$ and 5-HT$_6$. Meanwhile, the compounds had very low % inhibition values of −12.4 to 13.5 against 5-HT$_{1E}$. The % inhibition values of the compounds against 5-HT$_6$ were greatly affected by the number (n) of carbon atoms of the alkyl chain between X and Y. Specifically, the compounds in which the alkyl chain consists of 5 carbon atoms had the highest % inhibition values. The % inhibition value decreased significantly with decreasing length of the alkyl chain. The compounds wherein X is CO showed higher % inhibition values against 5-HT$_7$, whereas the compounds wherein X is CH$_2$ showed higher % inhibition values against 5-HT$_6$.

TABLE 2

| Example No. | Y (structure) | 5-HT$_7$ % inhibition | 5-HT$_7$ Ki (nM) | 5-HT$_{2C}$ % inhibition | 5-HT$_{2C}$ Ki (nM) | 5-HT$_6$ % inhibition | 5-HT$_6$ Ki (nM) |
|---|---|---|---|---|---|---|---|
| Example 2.9 | 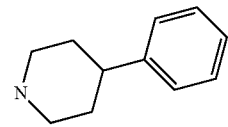 [SMILES: c1ccc(C2CCNCC2)cc1] | 99.8 | 157 | 55.3 | 758 | 92.2 | 373 |
| Example 2.25 | | 96.0 | 153 | 53.2 | 905 | 67.0 | 1496 |
| Example 2.43 | | 89.9 | 212 | — | — | 94.9 | 169 |
| Example 2.50 | | 94.1 | 178 | — | — | 96.1 | 123 |
| Example 2.54 | | 94.4 | 205 | — | — | 55.5 | 1429 |
| Example 2.57 | | 91.1 | 353 | — | — | 32.9 | — |
| Example 2.10 | 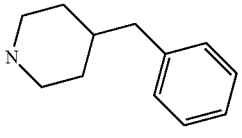 [SMILES: c1ccc(CC2CCNCC2)cc1] | 102.9 | 252 | 70.4 | 683 | 91.9 | 354 |
| Example 2.26 | | 97.4 | 312 | 43.1 | — | 93.4 | 302 |
| Example 2.44 | | 86.8 | 232 | — | — | 97.8 | 142 |

TABLE 3

| Example No. | Y (structure) | 5-HT$_7$ % inhibition | 5-HT$_7$ Ki (nM) | 5-HT$_{1A}$ % inhibition | 5-HT$_{2C}$ % inhibition | 5-HT$_6$ % inhibition |
|---|---|---|---|---|---|---|
| Example 2.12 | 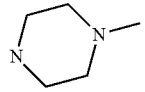 | 50.0 | 1910 | 5.5 | 82.5 | 77.6 |
| Example 2.28 | | 40.4 | — | 15.9 | — | 78.4 |
| Example 2.46 | | 49.4 | — | 19.3 | — | 82.2 |
| Example 2.11 | 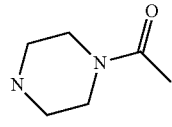 | 72.1 | 2336 | 51.8 | 51.3 | 24.5 |
| Example 2.27 | | 64.6 | 1072 | 25.4 | 6.6 | 13.8 |
| Example 2.45 | | 63.1 | 1485 | 6.2 | — | 35.0 |

TABLE 3-continued

| Example No. | Y (structure) | 5-HT$_7$ % inhibition | 5-HT$_7$ Ki (nM) | 5-HT$_{1A}$ % inhibition | 5-HT$_{2C}$ % inhibition | 5-HT$_6$ % inhibition |
|---|---|---|---|---|---|---|
| Example 2.13 | | 94.8 | 127 | 76.8 | 72.3 | 57.9 |
| Example 2.29 | | 92.0 | 282 | 66.5 | 38.0 | 57.4 |
| Example 2.32 | | 90.8 | 404 | 69.4 | — | 14.7 |
| Exmaple 2.47 | | 86.0 | 602 | 62.0 | — | 77.5 |
| Example 2.51 | | 86.8 | 233 | 74.9 | — | 65.1 |
| Example 2.58 | | 88.7 | 404 | 64.9 | — | 15.1 |
| Example 2.14 | | 94.1 | 73 | 80.5 | 63.7 | 81.3 |
| Example 2.15 | | 100.3 | 38 | 94.2 | 73.5 | 85.3 |
| Example 2.30 | | 98.7 | 86 | 102.2 | — | 62.6 |
| Example 2.33 | | 97.0 | 50 | 100.9 | — | 16.1 |
| Example 2.48 | | 90.5 | 89 | 105.2 | — | 96.9 |
| Example 2.52 | | 94.4 | 31 | 102.6 | — | 95.5 |
| Example 2.55 | | 95.8 | 55 | 103.2 | — | 77.8 |
| Example 2.59 | | 94.7 | 96 | 104.7 | — | 21.7 |
| Example 2.16 | | 102.0 | 74 | 108.0 | 55.8 | 30.7 |
| Example 2.31 | | 99.6 | 30 | 103.2 | 62.6 | 44.4 |
| Example 2.34 | | 97.7 | 33 | 103.6 | 74.2 | 51.5 |
| Example 2.49 | | 85.7 | 145 | 104.7 | — | 85.1 |
| Example 2.53 | | 91.5 | 65 | 101.1 | — | 75.5 |
| Example 2.56 | | 92.5 | 64 | 104.5 | — | 56.3 |
| Example 2.60 | | 90.7 | 155 | 102.7 | — | 12.2 |

Referring to the results in Table 3, the compounds wherein Y a piperazinyl groups whose nitrogen atom is substituted with alkyl (R$_5$) showed good inhibitory effects on 5-HT$_{2C}$ and 5-HT$_6$ together with 5-HT$_7$. On the other hand, the compounds wherein R$_5$ is an aryl group, a heteroaryl group or benzyl showed good inhibitory effects on 5-HT$_{1A}$ as well as 5-HT$_{2C}$ and 5-HT$_6$, together with 5-HT$_7$. Particularly, the compounds wherein R$_5$ is an aryl group showed excellent inhibitory effects on 5-HT$_{1A}$. On the other hand, the compounds in which the alkyl chain consists of 5 carbon atoms had the highest % inhibition values against 5-HT$_6$, as in the results in Table 2. The % inhibition value decreased significantly with decreasing length of the alkyl chain. The compounds wherein X is CO showed higher % inhibition values against 5-HT$_7$, whereas the compounds wherein X is CH$_2$ showed higher % inhibition values against 5-HT$_6$.

Referring to the results in Tables 1-3, when Y has a structure within the range defined above and X is CH$_2$ irrespective of the structure of Y, the compounds wherein n is 5 showed lower % inhibition values against the 5-HT$_7$ receptor compared to the compounds wherein n is from 2 to 4. The compounds wherein n is 5 have a carbazole-(CH$_2$)$_5$—Y structure in which X (CH$_2$) is connected to the alkyl chain ((CH$_2$)$_5$). This structure is estimated to lower the % inhibition values of the compounds wherein n is 5 against the 5-HT$_7$ receptor.

In order to investigate the inhibitory effect of the length of the alkyl chain between the carbazole moiety and the tertiary amine (Y) on the 5-HT$_7$ receptor when n is greater than 5, the compounds wherein n is 6 and the compounds wherein n is 7 were prepared (Comparative Examples 1-6).

<Comparative Example 1>

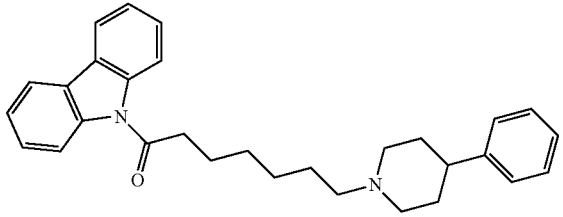

<Comparative Example 2>

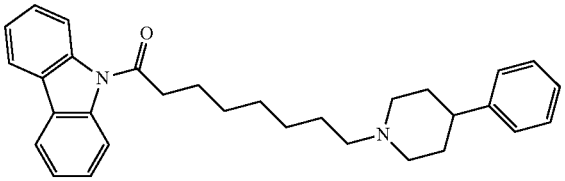

<Comparative Example 3>

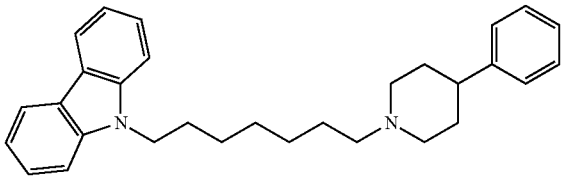

-continued

<Comparative Example 4>

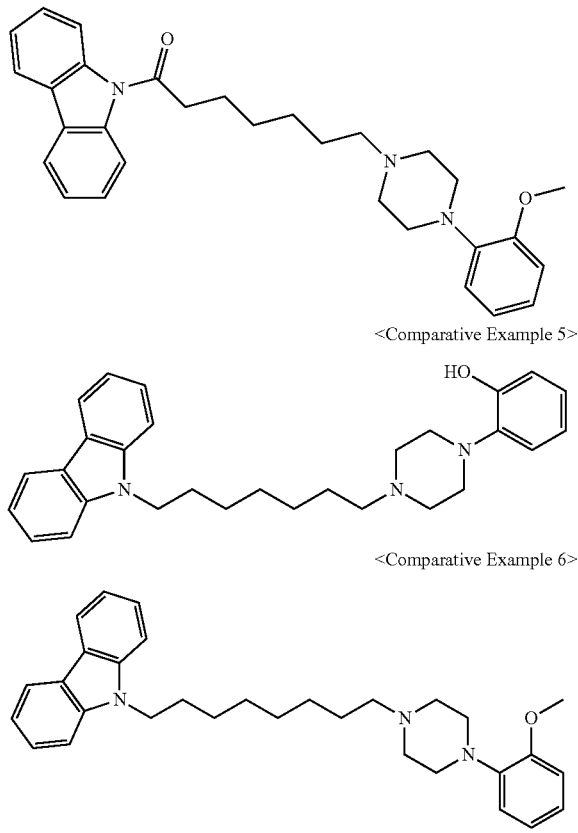

<Comparative Example 5>

<Comparative Example 6>

The compound of Comparative Example 1 wherein Y is 4-phenylpiperidyl, X is CO, and n is 6 and the compound of Comparative Example 2 wherein Y is 4-phenylpiperidyl, X is CO, and n is 7 were measured to have % inhibition values of 47.5 and 32.8 against the 5-HT$_7$ receptor, respectively, which were lower than those of the compounds of Examples 2.9 and 2.25 shown in Table 2. The compound of Comparative Example 3 wherein Y is 4-phenylpiperidyl, X is CH$_2$, and n is 6 was measured to have a % inhibition value of 42.7 against the 5-HT$_7$ receptor, which was lower than that of the compound of Example 2.43 shown in Table 2.

The compound of Comparative Example 4 wherein Y is 2-methoxyphenylpiperazinyl, X is CO, n is 6, the compound of Comparative Example 5 wherein Y is 2-methoxyphenylpiperazinyl, X is CH$_2$, and n is 6, and the compound of Comparative Example 6 wherein Y is 2-methoxyphenylpiperazinyl, X is CH$_2$, and n is 7 were measured to have % inhibition values of 44.5, 42.7, and 19.7 against the 5-HT$_7$ receptor, respectively, which were lower in efficacy than those of the inventive compounds wherein Y is 2-methoxyphenylpiperazinyl shown in Table 3.

From these results, it can be seen that the compounds wherein n is from 2 to 5 can effectively act on the 5-HT$_7$ receptor. Particularly, the compounds wherein n is 7 or greater had considerably low % inhibition values, making it substantially difficult to apply the compounds as antagonists against the 5-HT$_7$ receptor, and therefore, they are not expected to be useful for the treatment or prevention of central nervous system diseases, such as depression, migraine, anxiety, pain, inflammatory pain, neuropathic pain, body temperature dysregulation, circadian rhythm dysregulation, sleep disturbance, and smooth muscle-related diseases.

Experimental Example 2: Antagonism Against Migraine

It is known that inflammatory proteins leaked from meningeal vessels by 5-HT are implicated in causing migraine. The amount of the proteins leaked in the presence of the compound of Example 2.10 was measured and the preventive effect of the compound on migraine was assessed by a partial modification of the method described in the literature [Rachel A. Spokes, Vicki C. Middlefell, European Journal of Pharmacology (1995) 281, 75-79]. SB-269970, which is known as a 5-HT$_7$ receptor antagonizing compound (J. Med. Chem. (2000) 43, 342-345), was used as a comparative compound. A negative control free of 5-HT$_7$ was prepared. The fluorescence intensity of the negative control was defined as a reference value. As a positive control, physiological saline was added instead of the compound of Example 2-10.

Rats (350-450 g) were administered urethane (1.5 g/kg) intraperitoneally. 50 mg/kg of a fluorescent protein (FITC-BSA) was administered intravenously through a cannula introduced into the saphenous vein, and 1 µM 5-HT$_7$ was administered intravenously. SB-269970 and the compound of Example 2.10 were administered intraperitoneally. The cerebral lobes were separated and the meninges were drawn from each rat. The meninges were allowed to stand at 37° C. for 16 h in the presence of physiological saline at pH 11, followed by centrifugation. The supernatant was plated on plates. The fluorescence intensity was measured using a fluorescence leader (excitation wavelength 485 nm, absorption wavelength 530 nm) and the meninges were weighed. The fluorescence intensity per mg of the meningeal proteins was calculated.

The 5-HT$_7$ receptor antagonizing compound SB-269970 reduced the amount of the proteins leaked by 10 mg/kg. Even when SB-269970 was administered at an increased dose of 30 mg/kg, the amount of the proteins leaked was not lowered down to the reference value. In contrast, when the compound of Example 2.10 was administered at a dose of 3 mg/kg, the amount of the proteins leaked was effectively suppressed to a level close to the reference value. The results are shown in FIG. 1.

When each of the compounds of Examples 2.4, 2.9, 2.14, 2.15, 2.31, and 2.55 was administered in an amount of 5 mg/kg to 20 mg/kg, the protein leakage was suppressed to a level close to the reference value.

These results lead to the conclusion that the inventive compounds can effectively inhibit migraine.

What is claimed is:
1. A carbazole derivative represented by Formula 1:

(1)

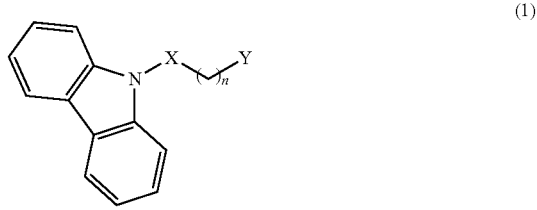

wherein X is C(O),

Y is piperazinyl groups in which the nitrogen atom is substituted with $R_5$, n is an integer from 2 to 5, and $R_5$ is selected from $C_1$-$C_6$ alkyl, $C_1$-$C_4$ alkylcarbonyl, phenyl substituted with $C_1$-$C_4$ alkyloxy, hydroxyphenyl, benzyl, benzoisoxazol-3-yl or a pharmaceutically acceptable salt thereof.

2. The carbazole derivative or pharmaceutically acceptable salt thereof according to claim 1, wherein Y is selected from 4-methylpiperazinyl, 4-acetylpiperazinyl, 4-(2-methoxyphenyl)piperazinyl, 4-(2-hydroxyphenyl)piperazinyl, 4-benzylpiperazinyl, and 4-(benzoisoxazol-3-yl)piperazinyl.

3. The carbazole derivative or pharmaceutically acceptable salt thereof according to claim 1, wherein the carbazole derivative represented by Formula 1 is selected from:

1-(9H)-carbazol-9-yl)-6-(4-methylpiperazin-1-yl)hexan-1-one;
6-(4-benzylpiperazin-1-yl)-1-(9H-carbazol-9-yl)hexan-1-one;
6-(4-benzo[d]isoxazol-3-yl)piperazin-1-yl)-1-(9H-carbazol-9-yl)hexan-1-one;
1-(9H-carbazol-9-yl)-6-(4-(2-hydroxyphenyl)piperazin-1-yl)hexan-1-one;
1-(9H-carbazol-9-yl)-6-(4-(2-methoxyphenyl)piperazin-1-yl)hexan-1-one;
5-(4-acetylpiperazin-1-yl)-1-(9H-carbazol-9-yl)pentan-1-one;
1-(9H)-carbazol-9-yl)-5-(4-methylpiperazin-1-yl)pentan-1-one;
5-(4-benzylpiperazinyl)-1-(9H-carbazol-9-yl)pentan-1-one;
1-(9H-carbazol-9-yl)-5-(4-(2-hydroxyphenyl)piperazin-1-yl)pentan-1-one;
1-(9H-carbazol-9-yl)-5-(4-(2-methoxyphenyl)piperazin-1-yl)pentan-1-one;
4-(4-benzylpiperazin-1-yl)-1-(9H-carbazol-9-yl)butan-1-one;
1-(9H-carbazol-9-yl)-4-(4-(2-hydroxyphenyl)piperazin-1-yl)butan-1-one; and
1-(9H-carbazol-9-yl)-4-(4-(2-methoxyphenyl)piperazin-1-yl)butan-1-one.

4. A pharmaceutical composition for preventing and treating a central nervous system disease, comprising a carbazole derivative represented by Formula 1:

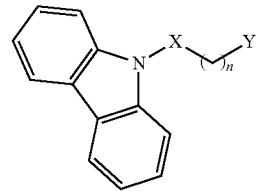

(1)

wherein X is or C(O),

Y is piperazinyl groups in which the nitrogen atom is substituted with R5, n is an integer from 2 to 5, and $R_5$ is selected from $C_1$-$C_6$ alkyl, $C_1$-$C_4$ alkylcarbonyl, phenyl substituted with $C_1$-$C_4$ alkyloxy, hydroxyphenyl, benzyl, benzoisoxazol-3-yl or a pharmaceutically acceptable salt thereof as an active ingredient.

5. The pharmaceutical composition according to claim 4, wherein the carbazole derivative represented by Formula 1 is selected from compounds represented by Formula 4:

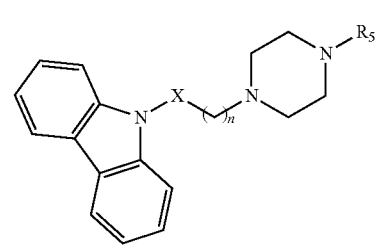

(4)

wherein X is C(O), n is an integer from 2 to 5, and $R_5$ is selected from $C_1$-$C_6$ alkyl, $C_1$-$C_4$ alkylcarbonyl, phenyl substituted with $C_1$-$C_4$ alkyloxy, hydroxyphenyl, benzyl, and benzoisoxazol-3-yl.

* * * * *